(12) United States Patent
Veiner et al.

(10) Patent No.: US 7,331,474 B2
(45) Date of Patent: Feb. 19, 2008

(54) SPECIMEN-CONTAINER RACK FOR AUTOMATED CLINICAL INSTRUMENT

(75) Inventors: Craig R. Veiner, Miami, FL (US); Frank M. Tappen, Plantation, FL (US); Roberto Del Valle, Coral Gables, FL (US); Richard A. Marquis, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 739 days.

(21) Appl. No.: 10/794,685

(22) Filed: Mar. 5, 2004

(65) Prior Publication Data

US 2005/0194333 A1    Sep. 8, 2005

(51) Int. Cl.
*A47B 73/00* (2006.01)
(52) U.S. Cl. .............................. 211/74; 211/77; 422/104
(58) Field of Classification Search .................. 422/99; 211/74, 77
See application file for complete search history.

(56) References Cited

U.S. PATENT DOCUMENTS

| | | | |
|---|---|---|---|
| 3,897,216 A | | 7/1975 | Jones |
| 4,040,533 A | | 8/1977 | De Boer et al. |
| 4,454,939 A | | 6/1984 | Kampf et al. |
| 4,982,553 A | * | 1/1991 | Itoh ............................ 53/246 |
| 5,008,082 A | | 4/1991 | Shaw |
| 5,135,387 A | * | 8/1992 | Martin et al. ................ 431/116 |
| 5,343,811 A | * | 9/1994 | Schuster ..................... 104/283 |
| 5,687,849 A | | 11/1997 | Borenstein et al. |
| 5,720,377 A | | 2/1998 | Lapeus et al. |
| 6,065,617 A | * | 5/2000 | Cohen et al. .................. 211/74 |
| 6,337,050 B1 | | 1/2002 | Takahashi et al. |
| 6,489,169 B1 | * | 12/2002 | Cohen et al. .................. 436/47 |
| 6,571,934 B1 | | 6/2003 | Thompson et al. |
| 7,000,785 B2 | * | 2/2006 | Jafari et al. .................... 211/74 |
| 7,018,587 B2 | * | 3/2006 | Heath et al. ................... 422/63 |

FOREIGN PATENT DOCUMENTS

DE    19501571 A1 *  9/1996

\* cited by examiner

*Primary Examiner*—Walter D. Griffin
*Assistant Examiner*—Imran Akram
(74) *Attorney, Agent, or Firm*—Warren W. Kurz; Mitchell E. Alter

(57) ABSTRACT

A magnetically-attractive specimen-container rack for use with a magnetic transport system for transporting racks of specimen-containers to or within an automated clinical instrument for analysis and/or processing. The specimen-container rack comprises a pair of U-shaped magnetically-attractive members mounted in the base section of the rack housing so that the distal ends of such members extend towards the base of the rack and terminate in a plane slightly short of the plane in which the rack is supported for movement atop a rack-supporting surface. Such members are adapted to cooperate with similarly-shaped permanent magnets carried by an X/Y-movable truck that underlies a non-magnetic rack-supporting plate. Other features of the rack include a pair of side-pockets formed in one side of the rack in the vicinity of the end walls of the rack housing, such pockets serving to receive a movably-mounted member associated with a linear drive mechanism by which the rack can be physically advanced edgewise along a linear path; and notch structure by which the rack can be releasably engaged by a movably-mounted plate which serves to lift and invert the rack to effect mixing of contained specimens.

10 Claims, 16 Drawing Sheets

SPECIMEN-CONTAINER RACK FOR AUTOMATED CLINICAL INSTRUMENT

CROSS-REFERENCE TO RELATED APPLICATIONS

Reference is made to the following patent applications filed concurrently herewith:

U.S. application Ser. No. 10/794,702 filed Mar. 5, 2004 entitled "Specimen-Transport Module for a Multi-Instrument Clinical Workcell", and U.S. application Ser. No. 10/794,686, now U.S. Pat. No. 7,028,831 issued Apr. 18, 2006 entitled "Magnetic Specimen-Transport System for Automated Clinical Instrument."

BACKGROUND OF THE INVENTION

1. Field of the Invention

The present invention relates to improvements in specimen-container racks of the type used to support multiple containers, e.g., test tubes, of liquid specimens for analysis or processing by a clinical instrument. More particularly, it relates to improvements in specimen-container racks of the type that are adapted to be transported over a rack-supporting surface via magnetic forces.

2. The Prior Art

It is known in the art to perform diagnostic tests on various liquid biological specimens, e.g., whole blood, serum, urine, spinal fluids, etc., using different automated clinical instruments. The specimens to be analyzed by such instruments are commonly collected in various types of test tubes or containers. Each container is normally sealed at its top by a puncturable rubber cap through which a movably-mounted aspiration probe of a clinical instrument can enter and withdraw a desired aliquot of specimen for processing. Typically, five or six specimen-containers, each bearing encoded patient and test information in the form of a bar code or the like, are supported for aspiration by a single rack or cassette. The rack serves to align, center and equally space the containers to simplify the required movement of the instrument's aspiration probe in order to gain access to the interior of each container. In some instruments, the aspiration probe is movably-mounted on the exterior of the instrument housing; with such instruments, an external specimen-transport device or module can be used to present specimen-container racks to a specimen-aspiration station or location where the aspiration probe can sequentially aspirate specimens from each container.

U.S. Pat. No. 5,720,377, filed in the names of Lapeus et al., discloses a specimen-transport module of the type noted above. The module operates to present individual racks of specimen-containers to an externally-accessible aspiration probe of an associated clinical instrument. The module generally comprises three interrelated trays, viz., (a) an elongated input tray that is adapted to receive and temporarily store a linear queue of specimen-container racks, (b) a movably-mounted process tray that is adapted to receive racks of specimen-containers, one at a time, from the input tray and to present them to a location for specimen-aspiration and testing, and (c) an elongated output tray that is adapted to receive processed racks one at a time from the process tray and to temporarily store such racks in a linear output queue for subsequent retrieval. The input and output trays are linearly aligned, end-to-end, and each tray is provided with linear guides that interact with features on the racks to align the received racks to form the respective linear queues in which the racks are arranged side-by-side (cf., end-to-end). The process tray is positioned adjacent to the input and output trays and extends parallel to these trays. Upon reaching a loading position in the input tray, the foremost rack in the input queue is physically urged, edgewise, out of the tray and into an awaiting empty slot of the processing tray. Upon processing each container in a rack contained by the processing tray, the latter is advanced linearly, parallel to the input and output trays, to a location where the processed rack can be physically pushed, again edgewise, into an empty space on the output tray. Another pusher mechanism then operates to push together all the racks in the output tray to form a closely-spaced output queue of racks arranged side-by-side.

In the above-noted patent disclosure, each of the racks of the input queue is forwardly advanced over the rack-supporting surface of the input tray by a magnetic transport system that underlies the input tray. The input tray is made of a nonmagnetic material (in this case, aluminum), and each specimen-container rack carries one or more (preferably two) magnetically-attractive members in its base portion. The magnetic transport system that underlies the input tray comprises a pair of parallel conveyor belts, each carrying a plurality of permanent magnets at equally spaced locations along the belt length. The belts are trained about spaced pulleys, and one reach of each of the belts is closely spaced from the underside of the input tray, extending in the intended direction of rack-travel, i.e., in a direction parallel to the linear guides on the tray. As the belts are driven along their respective endless paths, the respective magnetic fields associated with two of the permanent magnets, one carried by each belt, passes through the input tray and approaches the rack from the side, at the two locations where the magnetically-attractive members are located. Upon reaching a position where the permanent magnets of the transport mechanism and the magnetically-attractive members of the racks become magnetically coupled, the racks slide along the surface of the input tray following the movement of the permanent magnets beneath the tray. The racks are thus magnetically advanced along a linear path defined by the rack's guides until the foremost rack in the input tray has reached a position in which it can be mechanically advanced edgewise into the process tray.

In the rack described above, the magnetically-attractive members are located in the rack's base portion in the vicinity of the ends of the rack. Each member is either tapered in thickness across the width of the rack or arranged at an angle with respect to the rack's bottom surface such that, as the permanent magnets of the conveyor belt system approach the rack from the side, the magnetic force between the magnets and the magnetically-attractive members gradually increases until the permanent magnets are either directly opposite the thickest portion of each of the magnetically-attractive members, or they are opposite to those portions of the members that are closest to the bottom surface of the rack and, hence, closest to the magnets (in both cases).

The specimen-container rack described above, while useful in a unidirectional magnetic transport system, is not well suited for use with a magnetic transport system adapted to transport racks in mutually perpendicular directions, i.e., in an X/Y plane. In an X/Y transport system, the magnetic force between the rack and transport system should be independent of the direction in which the rack is to be transported, rather than being optimized for transport in one direction only.

SUMMARY OF THE INVENTION

In view of the foregoing discussion, an object of this invention is to provide a specimen-container rack of the type described above that is readily adapted to be transported by a magnetic transport system in mutually-perpendicular directions atop a non-magnetic plate within a specimen-transport apparatus.

Another object of this invention is to provide a specimen-container rack that is adapted to be transported by either of two different independent transport systems of a specimen-transport module.

Another object of this invention is to provide a specimen-container rack with structure by which the rack may be releasably engaged by a specimen-mixing mechanism that operates to repeatedly invert the rack to effect specimen-mixing.

According to a first aspect of this invention, a specimen-container rack comprises housing having an upper section for receiving, aligning and equally-spacing a plurality of specimen-containers, and a base section for supporting the top portion. The base section further supports a pair of U-shaped members comprising a magnetically-attractive material. Such members are arranged at spaced locations on the base section, and each member comprises a pair of spaced leg members connected at one end by an integral bridging portion which interconnects the leg portions. The base section of the rack defines a planar bottom surface that, in use of the rack, is arranged juxtaposed to a rack-supporting surface of a specimen-transport apparatus. The U-shaped members are supported by the base section such that the respective leg members depend downwardly towards the bottom surface of the base section, and so that the distal ends of each of the leg members are substantially co-planar with the plane of such surface. The spacing between the respective leg members of the U-shaped members is such as to complete a magnetic circuit between a pair of correspondingly spaced permanent magnets carried by a magnetic transport mechanism that underlies the rack-supporting surface of the specimen-transport apparatus.

According to a second aspect of the invention, a specimen-container rack of the above type is provided with structure adjacent its opposing end walls by which a moving mechanism associated with the specimen-transport apparatus can physically engage a rack and advance such rack along a linear path atop the rack-supporting surface.

According to a third aspect of the invention, a rack of the above type is provided with structure on a side wall that interacts with complimentary structure on a movably-mounted plate of a mixing device that enables the rack to be lifted from its supporting surface and inverted for the purpose of mixing liquid specimens within sealed containers carried by such rack.

Being able to be magnetically transported over a supporting surface in mutually perpendicular directions, the specimen-container rack of the invention is much more versatile in its application than previous racks that are designed for linear movement in only one direction.

The invention and its various aspects and advantages will be better understood from the ensuing detailed description of preferred embodiments, reference being made to the accompanying drawings in which like reference characters denote like parts or components.

DETAILED DESCRIPTION OF PREFERRED EMBODIMENTS

The specimen-container rack of the invention is especially useful with a stand-alone specimen-transport module of the type described in the above-referenced U.S. application Ser. No. 10/794,702 filed Mar 5, 2004 entitled "Specimen-Transport Module for a Multi-Instrument Clinical Workcell." It will be appreciated, however, that the invention is also useful in stand-alone clinical instruments in which the specimen-transport system is an integral part of the instrument, rather than an accessory to the instrument.

Figure 1:
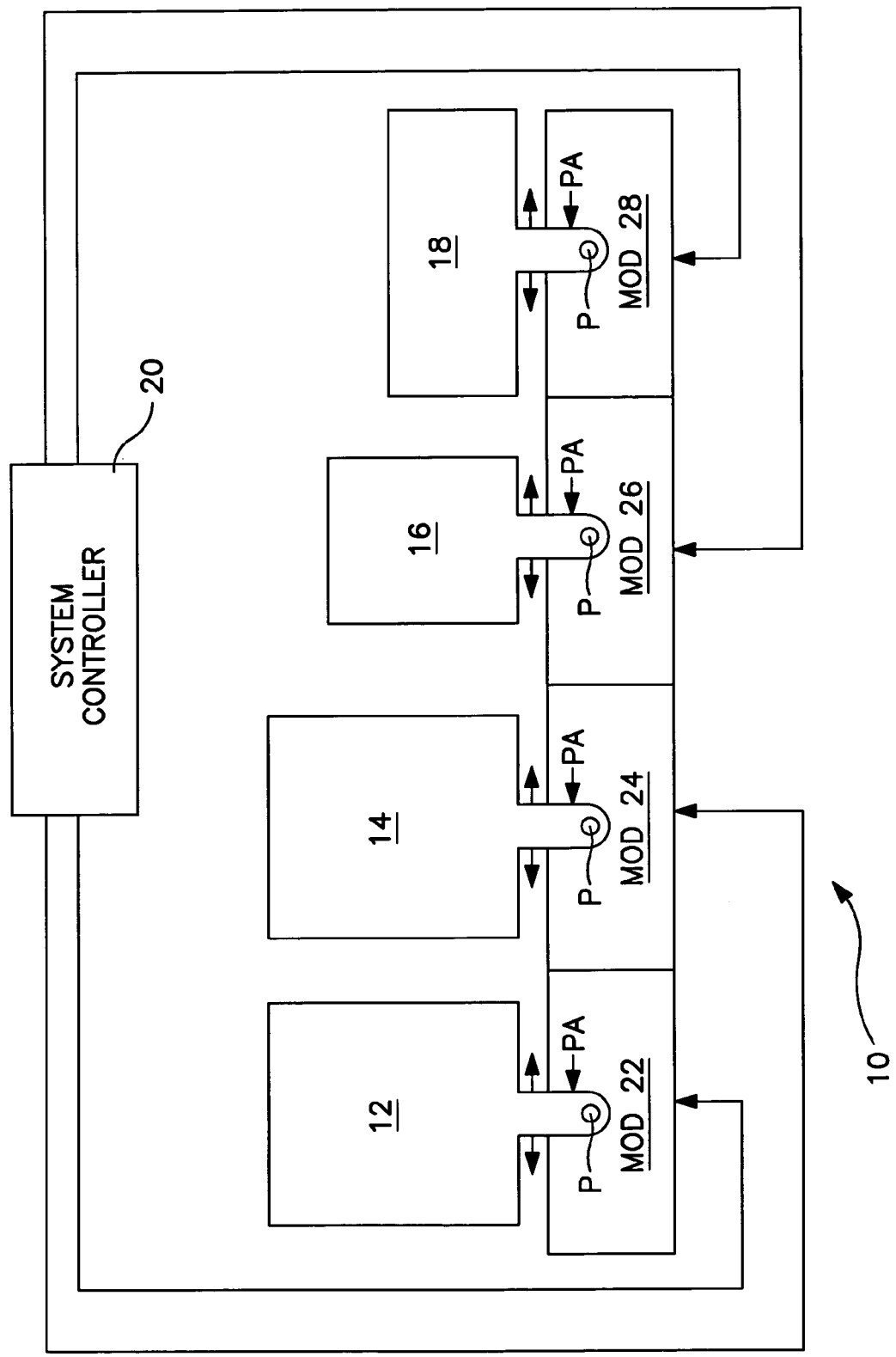
FIG. 1 is a schematic illustration of a multi-instrument clinical workcell in which the present invention is especially useful.

Referring now to the drawings, FIG. 1 schematically illustrates a multi-instrument workcell 10 that is adapted to analyze and/or otherwise process a whole blood specimen presented to it. Each of such specimens is contained by a test tube or other container C that is supported, together with additional containers, in a generally upright orientation and in a linear array, by a specimen-container rack R (shown and described in detail below with reference to in FIGS. 10, 11A, 11B, 12 and 14). In the workcell shown in FIG. 1, four separate clinical instruments 12, 14, 16 and 18, operate under the control of a common, microprocessor-based, system controller 20. Instruments 12 and 14 may be, for example, hematology instruments that operate, in a conventional manner, to differentiate and count the constituent blood cells of the whole blood specimen on the basis of DC volume, RF— conductivity and/or light scatter measurements made on each cell as it passes through the sensing aperture of a conventional flow cell. Instrument 14 may be, for example, a fluorescence flow cytometer that operates, in a conventional manner, to differentiate cell types based on the combination of fluorescence measurements and either light-scatter, DC volume or RF conductivity measurements made on each cell as it is made to pass through the sensing zone of an optical flow cell. Instrument 18 may be, for example, a slide-maker/slide-stainer device that produces and subsequently stains a smear of specimen on a microscope slide that can be subsequently analyzed under a microscope. While these clinical instruments can substantially differ in both the tasks they perform and in their mechanical make-up, each instrument has in common a movably-mounted aspiration probe assembly PA that is mounted on the exterior of the instrument housing and, hence, is accessible for the presentation of specimen containers ready for aspiration. The probe assemblies are mounted for movement both vertically (into the plane of the drawing) so as to enter a specimen-container presented to it in order to aspirate a small volume of the contained specimen for processing, and laterally (as indicated by the arrows) so as to enter any one of the specimen-containers supported by a specimen-container rack.

Workcell 10 further comprises a plurality of identical specimen-transporting modules (MOD 22, MOD 24, MOD 26 and MOD 28), one being operatively connected to, or otherwise associated with, each of the four clinical instruments 12, 14, 16 and 18. Each of the specimen-transporting modules provides at least two functions: Firstly, it functions to satisfy all specimen-presentation needs of the instrument with which it is directly associated, i.e., it functions (i) to receive multiple racks of specimen containers manually delivered to an input buffer of the module, (ii) to selectively transport such racks from the input buffer to a specimen-aspiration station at which all of the specimen containers of a given rack are accessible to the aspiration probe assembly of the associated instrument, and (iii) to deliver a rack to an output buffer following a desired specimen aspiration from all or selected ones of the containers in the rack. Upon being delivered to the output buffer, a rack, may be advanced to an off-loading position where it can be manually removed from the module or, alternatively, it may be returned to the specimen-aspiration station for reflex or repeat testing, as may be the case if a first test result indicates that a second aspiration of a given sample is required, or if a first test result is clearly erroneous. Secondly, each of the specimen-transporting modules functions to transfer racks of specimen-containers between adjacent modules associated with other clinical instruments, thereby enabling all instruments of the workcell to process a given specimen without need for any independent specimen-transfer mechanism, e.g., a robotic arm, or a conveyor system. To provide the latter function, each of the modules is rigidly connected to adjacent modules, thus enabling the modules to pass specimens back and forth, as described below with particular reference to FIG. 6. Preferably, each of the specimen-transport modules further provides a third function, namely, that of preparing a specimen for subsequent processing. Such sample-preparation is achieved by a specimen-mixing device that operates to repeatedly invert a specimen-container rack presented to it, thereby repeatedly inverting and mixing the contained specimens.

Figure 2:
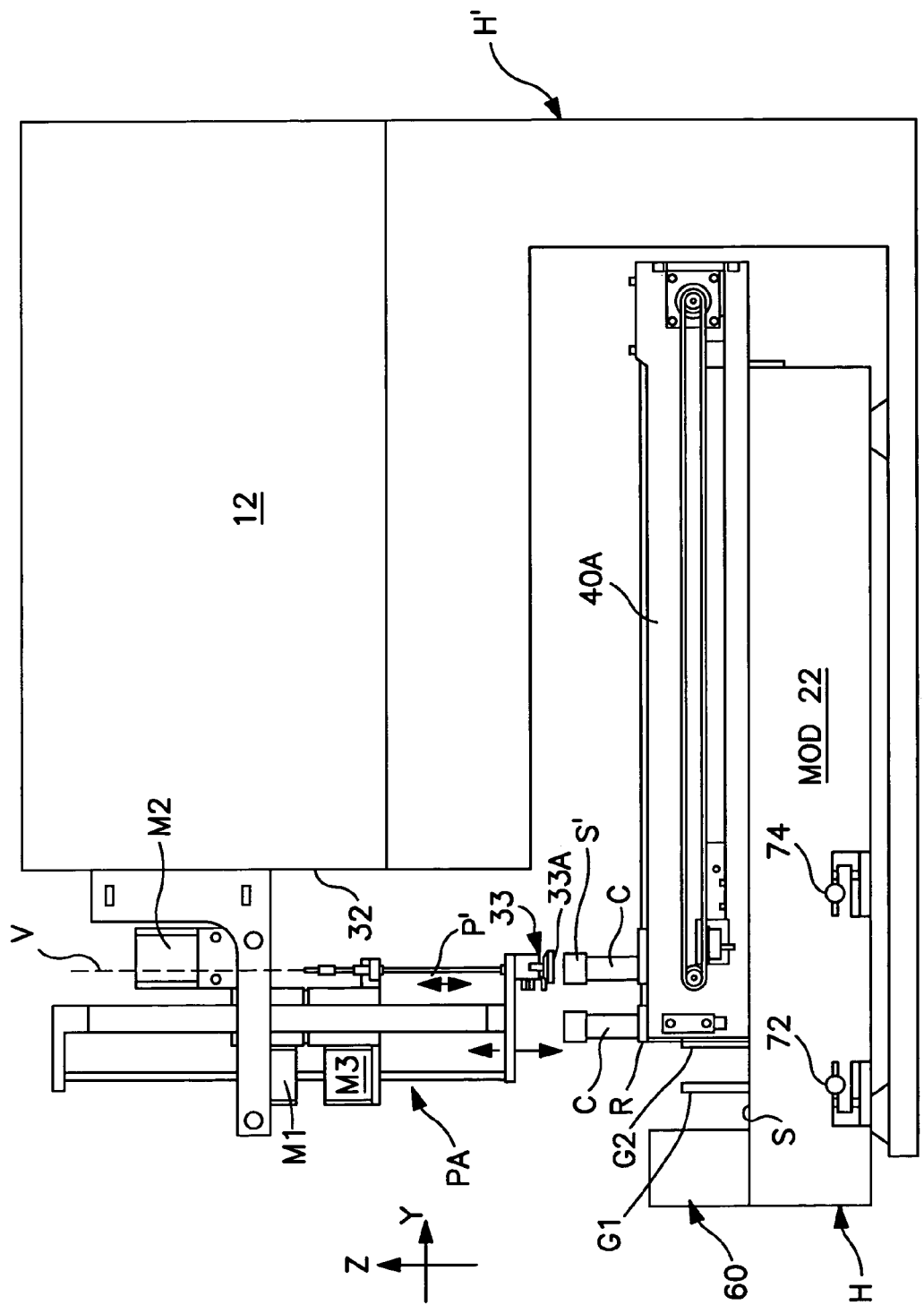
FIG. 2 is a side illustration of a specimen-transport module in combination with a clinical instrument.

In the side illustration of FIG. 2, the relationship between a specimen-transport module, e.g., MOD 22, and its associated clinical instrument, in this case instrument 12, is shown. To minimize the space requirements of the module/instrument combination, the instrument is designed to enable a major portion of the module housing H to underlie the main housing H' of the clinical instrument. The instrument's aspiration probe assembly PA extends forwardly of the front wall 32 of the instrument housing, and the specimen-transport module operates to selectively support a specimen-container rack R in an aspiration position 50 (shown in FIG. 3) so that the specimen-containers C supported by the rack are arranged in a common vertical plane V that coincides with the plane of vertical movement of the aspiration probe P'. The structural and operational details of the probe assembly are well understood and form no part of the invention. Briefly, however, movement of the probe assembly is controlled by three stepper motors, M1, M2 and M3, which operate under the control of the system controller 20. Stepper motor M1 operates to move the aspiration probe and a stripper mechanism 33 in a vertical plane, i.e., along the Z coordinate in FIG. 2, whereby the bottom surface 33A of the stripper mechanism can be moved downwardly into contact with the top surface of a rubber seal S' that encloses the top of the specimen container containing the sample to be aspirated. Stepper motor M3 then operates to control the vertical position of the aspiration probe P' of the probe assembly, whereby the probe tip can be driven downwardly so as to puncture the seal S' and enter the container for the purpose of aspirating a volume of specimen from within the container. Following specimen aspiration, motor M3 then operates to raise the aspiration probe out of the container. As the probe moves upwardly, the stripper mechanism 33 is held stationary and in contact with the seal S', thereby resisting the tendency of the upwardly-moving aspiration probe to lift the container out of the rack as a result of the frictional forces between the container seal and the aspiration probe. After the probe tip clears the top of the container seal, motor M1 operates to lift both the stripper mechanism and the aspiration probe to a vertical position in which the stripper mechanism is well clear of the container seal. The third stepper motor M2 operates to selectively advance the probe assembly laterally, i.e., in a horizontal plane, whereby the aspiration probe may access any one of the specimen containers supported by a rack located at an specimen-aspiration station 50, shown in FIG. 3.

Figure 3:
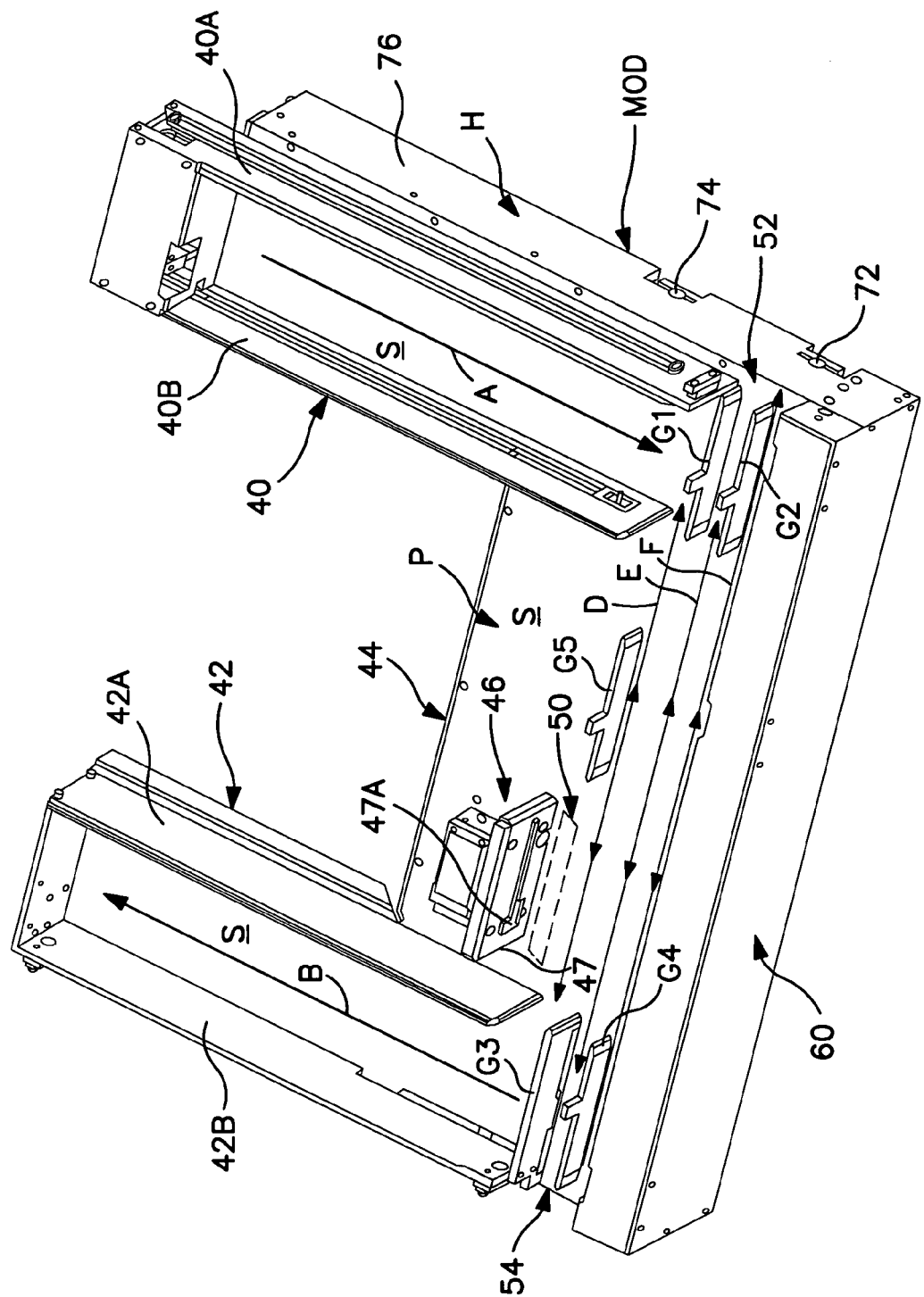
FIG. 3 is a perspective illustration of a specimen-transport module embodying the present invention.
Figure 4:
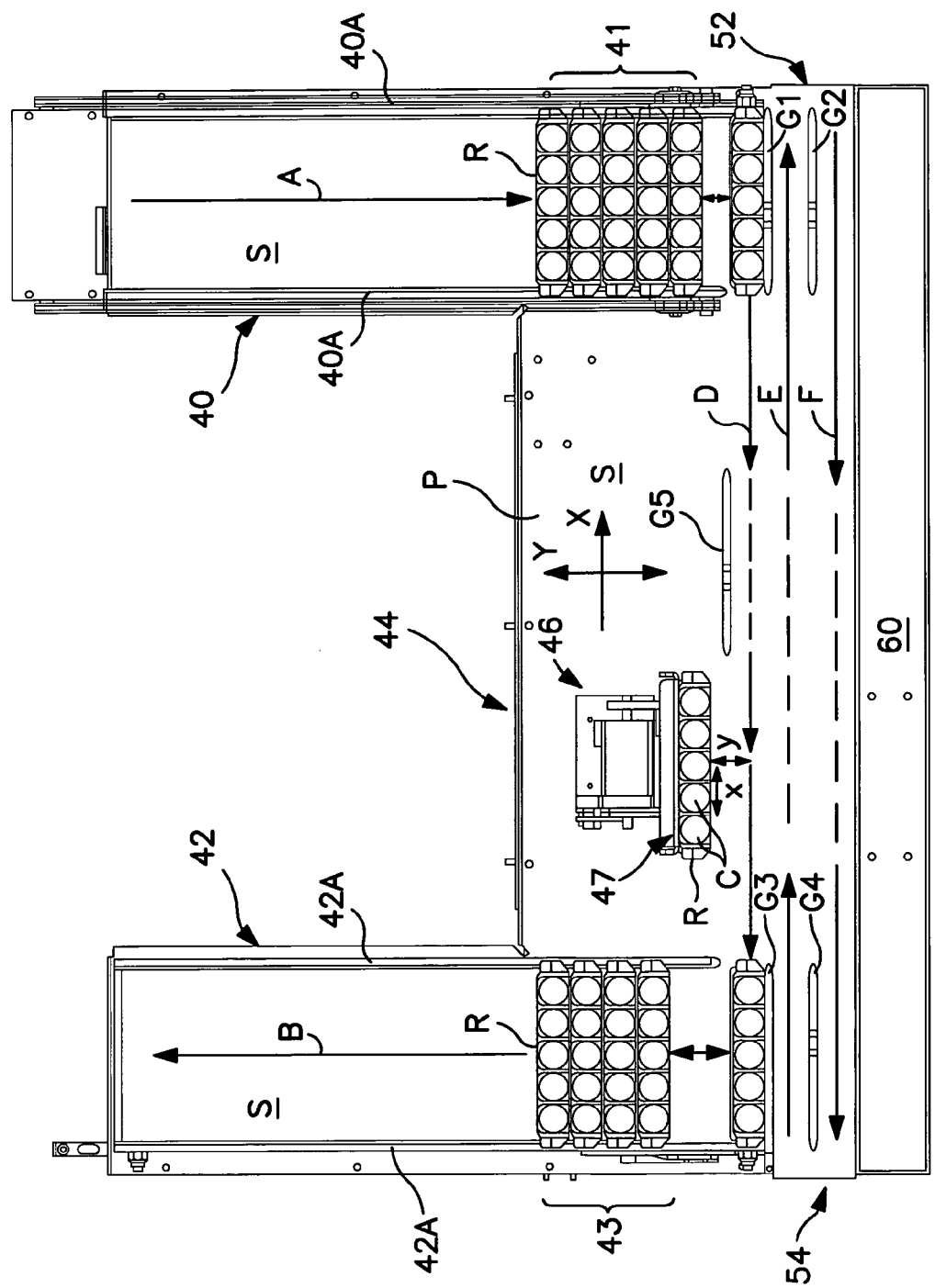
FIGS. 4 and 5 are top and front views, respectively, of the apparatus shown in FIG. 3, further illustrating the spatial positions of various specimen-container racks transported by such apparatus.
Figure 5:
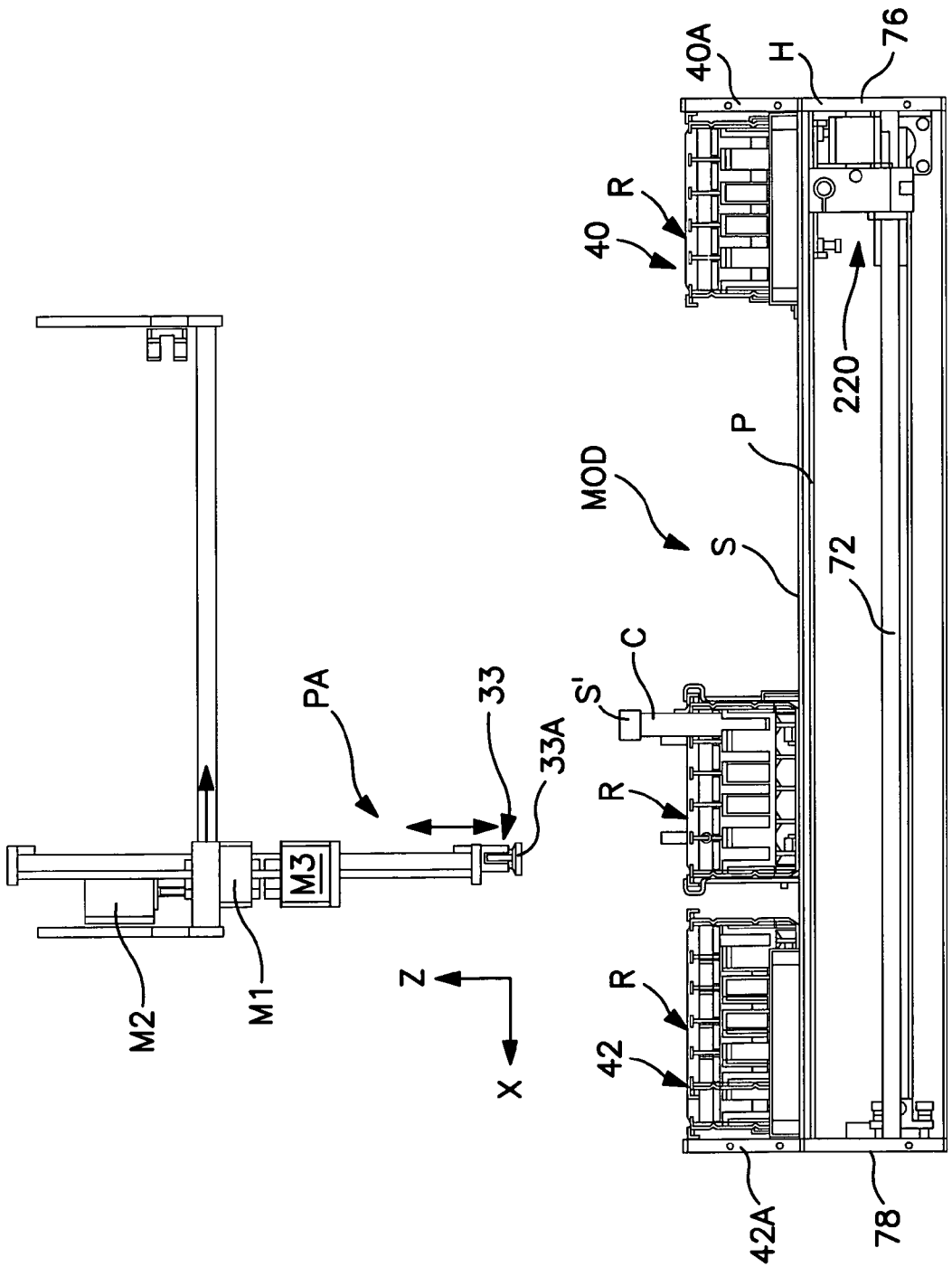
Figure 10:
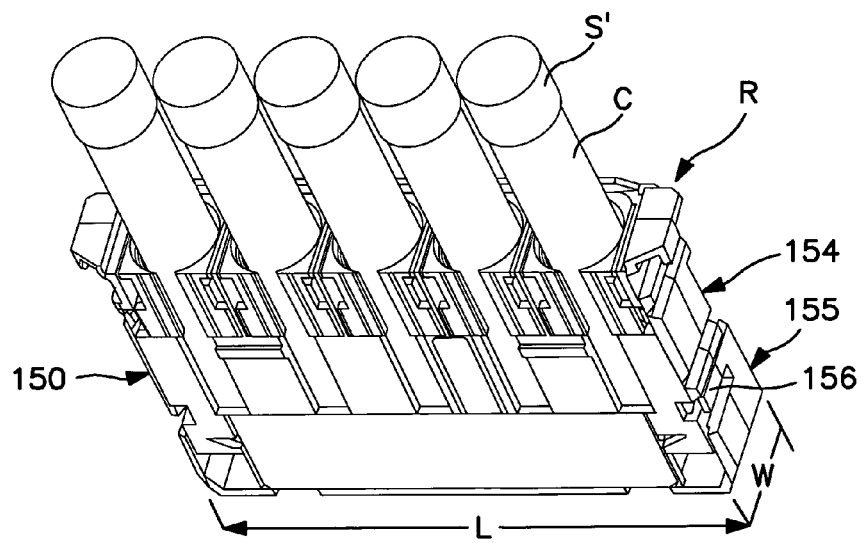
FIG. 10 is a perspective view of a specimen-container rack containing a plurality of specimen containers.

Referring additionally to FIGS. 3 and 4, each of the specimen-transport modules shown in FIG. 1 comprises a U-shaped housing H that defines (i) an input buffer 40 that is adapted to receive and support up to, say, twenty of the specimen-container racks R of the type shown in FIG. 10; (ii) an output buffer 42 in which racks of specimen-containers are accumulated after their respective specimens have been processed; and (iii) a specimen-processing section 44 through which individual racks of specimen-containers are advanced to appropriately position the racks for specimen-aspiration and/or mixing, or for transfer to an adjacent module. While racks within the input and output buffers are constrained to move along linear paths, respectively indicated by arrows A and B in FIGS. 3 and 4, racks passing through the processing section 44 are not so constrained. In fact, they are required to move along various mutually perpendicular paths in the X/Y plane (as indicated by the X/Y coordinates in FIG. 4) in order for the module to provide the specimen presentation and transfer functions noted above.

In presenting a rack of specimen-containers to the aspiration station 50 for processing, a rack will be conveyed forwardly (i.e., from right to left, as viewed in the drawings) along the specimen-processing path D which extends parallel to the X-coordinate. Upon reaching a position approximately opposite the specimen-aspiration station 50, the rack is moved rearwardly, i.e., towards the rear of the module in the Y direction, until it contacts a mounting plate 47 associated with a specimen-mixing device 46. As illustrated in FIG. 4, the distance y traveled in the Y-direction is somewhat greater than the width W of a rack, thereby enabling another rack to pass along path D without interference from a rack positioned adjacent the mounting plate 47. Upon contacting the plate 47, the rack is moved forwardly again, in the X-direction, by a short distance x. In moving as described, the rack is precisely located at the aspiration station 50 and the containers are then in a position to be accessed by the aspiration probe assembly of the associated clinical instrument. Moreover, during the short movement of the rack in the X-direction, the rack becomes securely mounted on the mounting plate 47 via a tongue-and-groove, described below. The mounting plate 47 of the mixing device is rotatably mounted and, as it rotates, it acts to lift and invert a rack secured to it, thereby mixing the specimens within the containers. (See, FIGS. 16A-16B.) Preferably, specimen-mixing is carried out immediately before each specimen is aspirated from a container, thus assuring a homogeneous specimen during aspiration. After aspirating one or all of the specimens in a rack, the rack is moved backwards along the same X/Y paths as described, thereby releasing the rack from the mounting plate 47 and returning the rack to the specimen-transport path D. The rack is then transported further along path D in the X-direction until it reaches a position opposite the output buffer 42. The rack is then moved into the output buffer by moving it rearwardly on surface S, in the Y-direction. In the event the test results from the rack last entered into the output buffer indicate that a test needs repeating, the rack is retrieved from the output buffer and is moved in the reverse direction along path D to a position upstream of the aspiration and mixing stations to await the completion of the processing of a rack then present at the aspiration station. After such processing is completed and the aspiration/mixing station 50 is vacated, the rack requiring reprocessing is again advanced to station 50 for processing.

In the event that tests need to be performed on a given specimen by another instrument in the workcell, a rack containing such specimen will be transported to either of the transport paths E or F which lead to specimen transfer stations 52 and 54 located on opposite sides of the module. At these stations, a rack can be transferred to a corresponding transfer station of an adjacent specimen-transport module in a multi-instrument workcell. The manner in which a rack is transferred from one module to another is described below with reference to FIG. 6.

Figure 6:
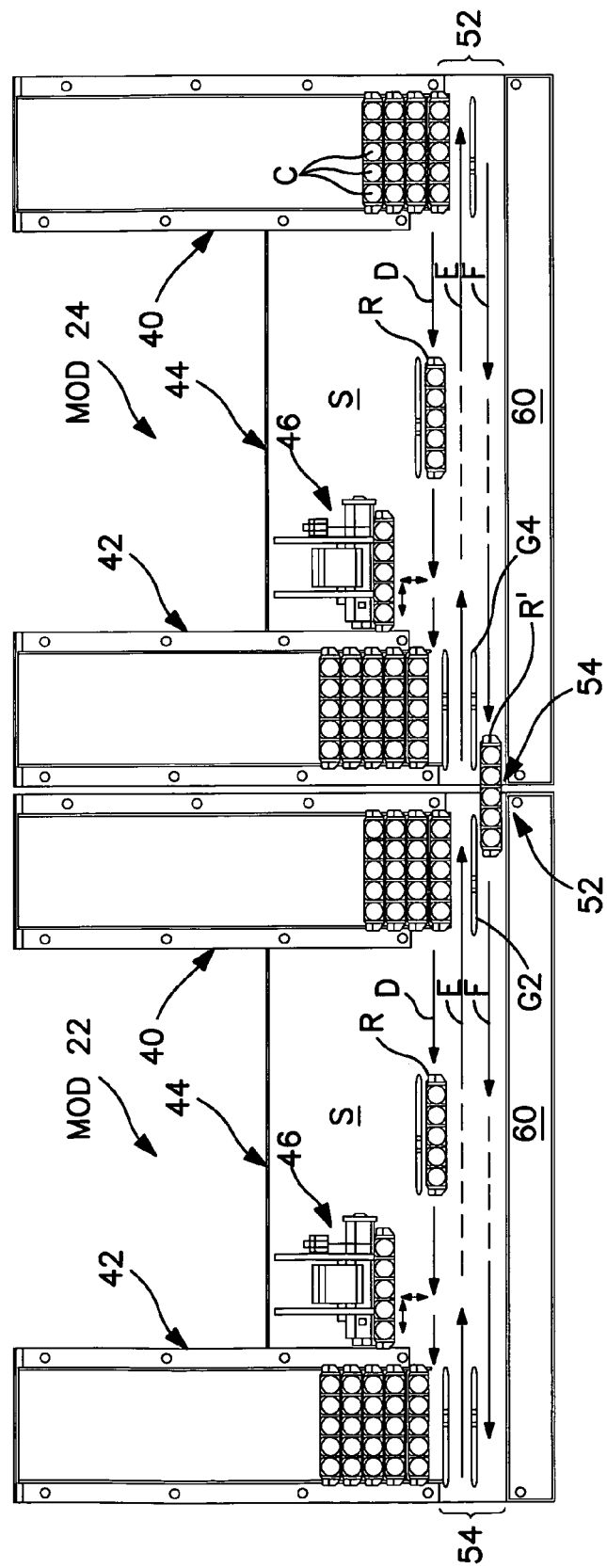
FIG. 6 is a top plan view of two adjacent specimen-transport modules of a multi-instrument workcell illustrating the transfer of a specimen-container rack from one module to another.

Referring to FIG. 6, two adjacent specimen transport modules, MOD 22 and MOD 24, are depicted during the process of transferring a specimen-container rack R' from MOD 24 to MOD 22. As shown, rack R' has been transported along path F to the rack-transfer station 54 of MOD 24, and to the corresponding path F of rack-transfer station 52 of MOD 22. As explained below, rack R' has been advanced to the "spanning" position shown by an X/Y magnetic transport system of MOD 24 that underlies the module's upper surface. Such a transport system operates to magnetically engage a rack at two locations in the rack's base portion where two magnetically-attractive members are mounted. Such members are spaced apart at opposite ends of the rack. To advance a rack to the position shown, i.e., where the rack spans two adjacent modules, a rack is first advanced to a position in which the rack's leading edge is approximately coincident with the edge of the module and the rack's side is adjacent guide member G4. The magnetic transport mechanism is then decoupled from the rack by moving the transport mechanism in the Y direction, towards guide member G3. Since the rack cannot follow the magnetic transport mechanism in this direction due to its engagement with guide G4, the magnetic coupling between the rack and transport mechanism will be overcome, and the rack will remain at the edge of the module. Thereafter, the magnetic transport mechanism will be repositioned to magnetically engage only one of the two magnetically-attractive members carried by the rack, i.e., the member more inboard from the module edge. The transport mechanism will then operate to advance the rack off the edge of MOD 24 and into the transfer station of the adjacent module MOD 22. The magnetic drive system of MOD 22 is then moved to a position in which it magnetically engages the rack at rack-transfer station 52 and transports it over the surface S of MOD 22 as required. It will be appreciated that rack-transfer between the specimen-transport modules can be effected on either of paths E or F, as determined by the system controller 20, which controls the traffic pattern of the racks throughout the module (and workcell). Preferably, however, one path is used to transfer racks in one direction, and the other path is used to transfer racks in the opposite direction. Not shown in the drawings is a pair of photoelectric sensors that detect the presence of a rack at each of the rack-transfer stations. When a rack that is to be transferred to another specimen-transport module is transported to either of the opposite end of paths E or F of a rack-transferring module, its presence is sensed by a sensor at the rack-transfer station of the transferring module. When a rack is also detected at the rack-transfer station by the sensor of the rack-receiving module, the rack is now in a spanning position to be acted upon by the X/Y rack-transport mechanism of the receiving module. The system controller acts on the output of these sensors to send the X/Y transport mechanism of the receiving module to further transport the rack therein.

Referring again to FIG. 3, the specimen-transport module housing H comprises a U-shaped top plate P comprising opposing leg portions P1 and P2, and an interconnecting base portion P3. The opposing leg portions P1 and P2 serve to support specimen-container racks in the input and output buffers 40 and 42. The base portion P3 serves to support racks for the above-described two-dimensional (X/Y) movement in the processing section 44. Plate P is a non-magnetic plate, preferably a non-magnetic stainless steel plate having a thickness of about 1.5 mm. The top surface of the plate is smooth, plane and featureless, and it is this surface that supports and slidingly engages the bottom pads of the specimen-container racks as the racks are moved along the various X- and Y-extending paths within the module. Each of the input and output buffers 40 and 42 comprises a pair of parallel side walls 40A, 40B and 42A, 42B, respectively. These walls extend upwardly from surface S and are spaced apart by a distance slightly greater than the length L of the specimen-container racks, whereby the rack may be received by the buffers and aligned as shown in FIG. 4. Two pair of upwardly-extending and parallel guides members, G1, G2, and G3, G4, are arranged on surface S at the rack-transfer stations 52 and 54 to assure that the racks are properly aligned (i.e., not skewed) on paths E and F during the transfer of racks between modules. Guide G1 further serves as a stop against which racks in the input buffer can be registered prior to being moved edgewise into the specimen-processing section along path D of the module. A fifth guide member G5 serves to properly align each rack as it approaches the specimen-aspiration station 50 along path D. At the front of housing H, i.e., adjacent path F of the module, an elongated housing 60 is provided that extends along the entire width of the module. As described below with reference to FIGS. 17 and 18, housing 60 contains a redundant drive mechanism that operates to physically engage and transport a specimen-container rack in either direction along path F of the specimen-transport module, whereby racks can be passed through, and thereby by-pass, a module in which the primary rack-transport mechanism, described below, is either busy or, for some reason, not operating.

Referring to the top view of FIG. 4, individual specimen-container racks are manually loaded at a loading station within the input buffer 40, typically to the rear of the last rack in the input queue 41, i.e., the rack farthest from the front housing 60. The racks are mechanically urged forwardly along the linear path A by a pair of opposing cam-actuated pusher members 62 (shown in FIG. 3) that are selectively driven forwards and backwards in linear slots 63 formed in the buffer side walls 40A. The pusher members are mounted for movement between an extended position (as shown in FIG. 3) in which they protrude from the side walls and engage a rack from both sides as the members are driven forwardly, towards the path D, and a retracted position in which they are recessed behind the side wall to enable the pusher members to move behind the last rack in the input queue in order to advance it, and the racks in front of it, forwardly. The mechanism for advancing the racks in the input buffer is described in detail in the above-referenced application Ser. No. 10/794,702 filed Mar. 5, 2004. A photo-sensor PS (e.g., a conventional photoelectric sensor that operates on the basis of a sensed reflectance signal) is mounted on top plate P at the forward end of the input buffer and serves to signal the system controller 20 when the foremost rack in the queue has reached a position adjacent to the guide member G1. Upon reaching this position, a rack is ready to be acted upon by the magnetic transport system of the invention which serves to transport racks of specimen containers through the specimen-processing section 44 of the module.

To advance the individual specimen-container racks along the various X and Y paths within the processing section 44 of the transport module, a magnetic transport system is provided. Such a system comprises a magnetic rack-transport mechanism 70 (shown in FIG. 7) that underlies the base portion P3 of the U-shaped non-magnetic plate P, and a plurality of magnetically-attractive specimen-container racks that are positioned atop the plate. As better explained below, the racks are rendered magnetically-attractive by mounting a pair of ferromagnetic members (shown in FIG. 12) in the rack's base portion at opposite ends. As explained below, mechanism 70 comprises a magnetic field-producing device, preferably in the form of a pair of permanent magnet assemblies. The permanent magnets are carried by a "truck" which is mounted for movement in the X/Y plane beneath and in close proximity to the bottom side of plate P. The magnetic field produced by each magnet passes through the non-magnetic support plate P of the transport module and magnetically couples with the magnetically-attractive members carried in the base portion of each specimen-transport rack. The magnetic bond between the magnets and magnetically-attractive members is sufficiently strong that, as the magnet-bearing truck moves in the X/Y plane beneath plate P, a magnetically-coupled rack atop the plate's upper surface S follows along.

Figure 7:
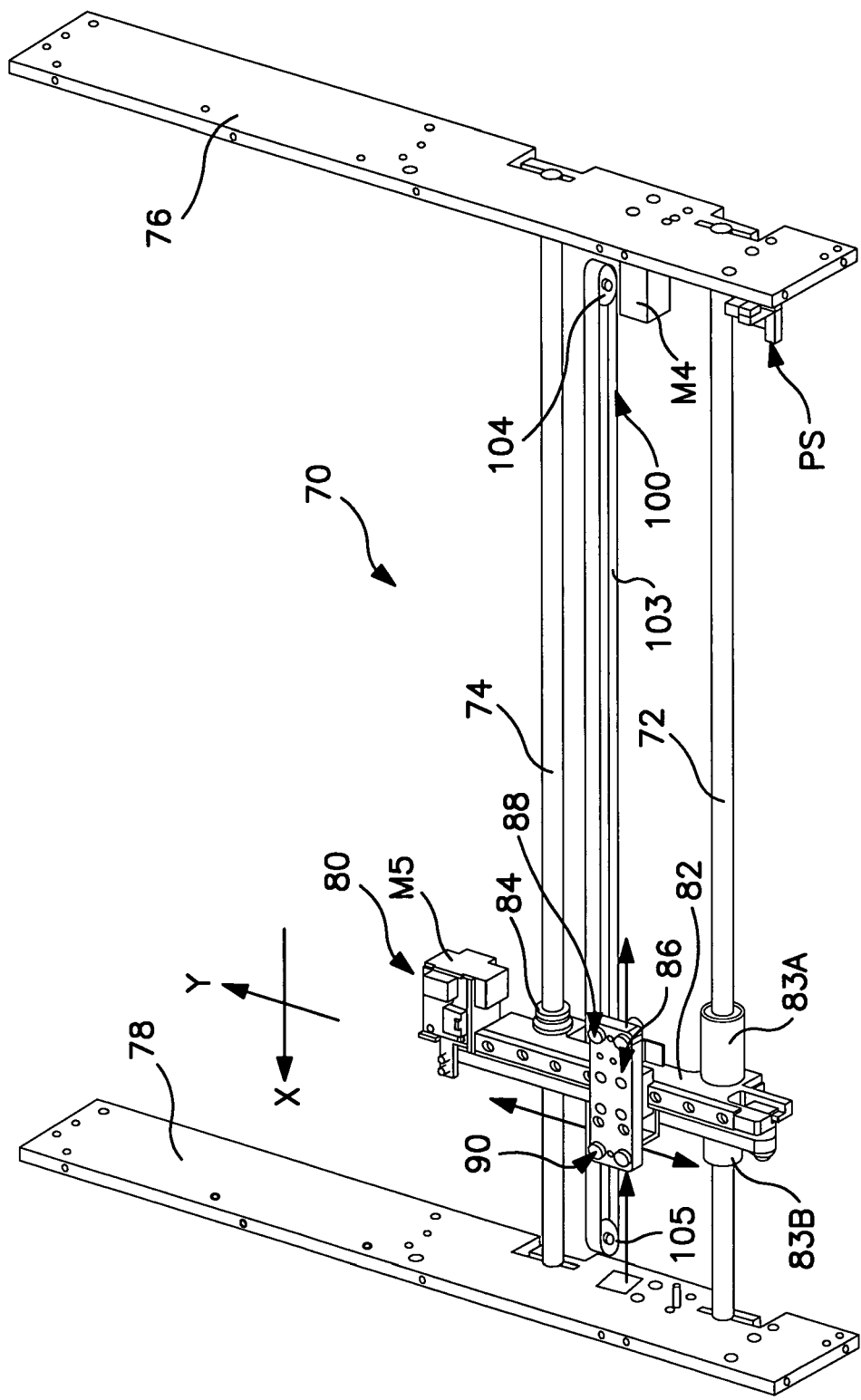
FIG. 7 is a perspective illustration of a preferred X/Y drive mechanism for controlling the X/Y position of individual specimen-container racks in the specimen-processing portion of the specimen-transport module shown in FIG. 1-6.

Referring now to FIG. 7, a preferred X/Y transport mechanism 70 is shown as comprising a pair of independent, bi-directional, linear drive mechanisms LD1 and LD2. One drive mechanism (LD1) serves to support the other (LD2) for movement along a first linear path parallel to the X-coordinate. LD1 also serves to selectively advance LD2 along such path in either direction. LD2, in turn, serves to support a magnetic field-producing device MD for movement along a second linear path extending perpendicular to the first linear path, i.e., in a direction parallel to the Y-coordinate; LD2 also serves to selectively advance the magnetic field-producing device in either direction along such second linear path. The second linear path is closely spaced from a bottom surface of the non-magnetic support plate, and the magnetic field-producing device is effective to produce a magnetic field atop the non-magnetic support plate that is sufficiently strong to magnetically engage the base portion of a rack positioned atop the support plate. Thus, as the magnetic field-producing device is advanced along the second linear path by LD2, and as LD2 is advanced along the first linear path by LD1, the rack moves atop the support plate in the X/Y plane and along the mutually perpendicular paths determined by the loads of LD1 and LD2. The structural particulars of the drive mechanisms are discussed below.

Figure 8A:
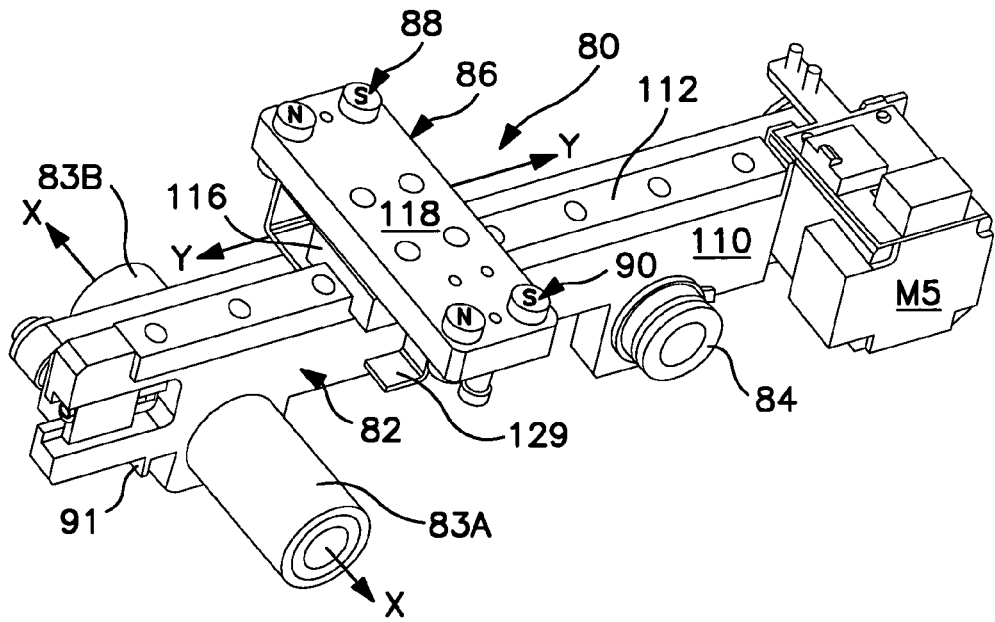
FIGS. 8A and 8B are enlarged perspective views of the Y-drive portion of the FIG. 7 apparatus.
Figure 8B:
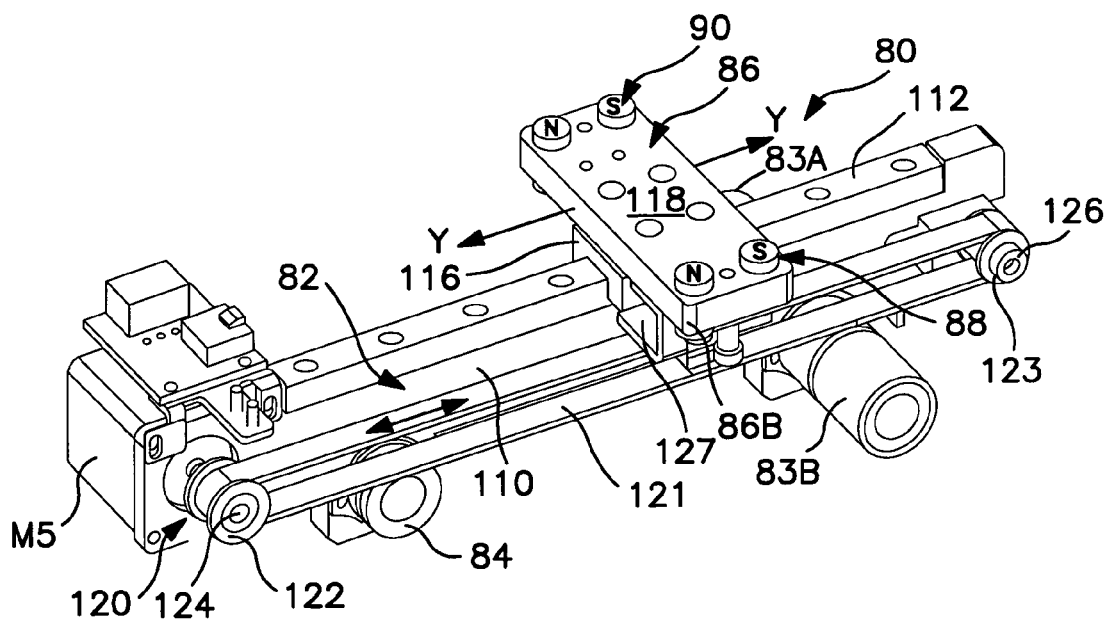

As shown in FIG. 7, linear drive mechanism LD1 comprises a pair of spaced and substantially parallel support shafts 72, 74 that are supported at their respective ends by the opposing side walls 76, 78 of the module housing H. A preferred spacing between shafts 72 and 74 is about 16 cm. As shown, shafts 72 and 74 extend parallel to the X coordinate and, together, they support the second linear drive mechanism LD2 for sliding movement parallel to the X coordinate. As best shown in FIGS. 8A and 8B, LD2 comprises an elongated housing 82 in which three sleeve bearings 83A, 83B and 84 are mounted. Bearings 83A and 83B are positioned on opposite sides of housing 82, and they are aligned to slide on shaft 72, the so-called "datum" shaft. The respective outboard edges of bearings 83A and 83B are relatively far apart, e.g., about 10 cm., to assure that the LD2 housing 82 remains perpendicular to the datum shaft at all times during its travel therealong. Bearing 84 is supported in a horizontal slot formed in housing 82, and this bearing rides along shaft 74 (the "anti-rotation" shaft) during movement of the LD2 housing in the X direction. The slot mounting enables bearing 84 to slide smoothly along the anti-rotation shaft even though the latter may not be perfectly parallel to the datum shaft; at the same time, however, the slot mounting prevents the LD2 housing from pivoting (about the datum shaft), thereby assuring that this housing remains in a horizontal (X/Y) plane at all times during movement of the truck assembly along the datum shaft. As explained below, the LD2 housing itself supports a permanent magnet-bearing truck 86 for sliding movement parallel to the Y coordinate. Preferably, truck 86 carries a pair of U-shaped magnets 88, 90 that magnetically interact and couple with a pair of magnetically-attractive members 170 (shown in FIG. 12) carried in the base portion of each specimen-container rack. As noted above, such magnetic interaction between the magnets and the magnetically-attractive members 170 is sufficiently strong to cause the specimen-container racks to slide across surface S and to follow the movement of the magnetic truck 86 beneath surface S.

As shown in FIG. 7, movement of the LD2 housing in the X direction (i.e., along shafts 72 and 74) is effected by a belt drive mechanism 100 mounted between the module housing walls 76 and 78. Drive mechanism 100 comprises an endless belt 103 that spans between a drive pulley 104 and idler pulley 105. Drive pulley 104 is rotatably driven by the drive shaft of an X-drive motor M4 mounted on housing wall 76. Motor M4 is a bi-directional stepper motor that operates under the control of the system controller 20. A tab 91 located at one end of the LD2 housing 82 is sensed by a photoelectric sensor (not shown) mounted on the module housing side wall 76 to provide a "home" position for the X-drive mechanism and a point of reference for the X-position of the magnetic truck 86.

Referring to FIGS. 8A and 8B, the LD2 housing 82 of the X/Y magnetic drive mechanism 70 comprises an elongated bar 110 in which the above-noted sleeve bearings 83A, 83B and 94 are mounted. Bar 110 supports a linear rail 112 along its uppermost surface. Rail 112 extends in a direction perpendicular to the respective longitudinal axes of the sleeve bearings; thus, when the sleeve bearings are mounted on their respective shafts, rail 112 extends parallel to the Y coordinate. Rail 112, in turn, slidably supports the above-noted permanent magnet-bearing truck 86. The latter comprises a channel-shaped member 116 which is adapted to slide along rail 112. Member 116 is rigidly connected to a non-magnetic plate 118 on which the permanent magnets 88 and 90 are mounted, as described below. As best shown in FIG. 8B, plate 118 is selectively driven along rail 112 by a second belt drive mechanism 120. The latter comprises an endless belt 121, a pair of pulleys 122, 123, and a bi-directional stepper motor M5 (the Y-drive motor) which communicates with and is controlled by the system controller 20 via a flex cable, not shown. Pulley 122 is rotatably driven by the drive shaft 124 of motor M5, and idler pulley 123 is mounted for rotation on a fixed shaft 126 extending from bar member 110. The respective axes of shafts 124 and 126 extend parallel to the X coordinate. Belt 121 is trained about the drive and idler pulleys as shown, and it is operatively connected to the magnetic truck assembly 94 by a bracket 127, best shown in FIG. 9. Thus, it will be appreciated that as the drive shaft of stepper motor M5 rotates, belt 121 advances over pulleys 123 and 123 and, owing to the connection of the belt and the magnetic truck assembly 94, the position of the permanent magnets carried by plate 118 in the Y direction is determined by the axial position of the stepper motor drive shaft. A flag member 129 depending from the bottom surface of plate 118 is sensed by a photoelectric sensor PS (shown in FIG. 7) mounted on side wall 76 of housing H to determine the "home" position of the Y-drive mechanism, and thus provides a point of reference for the Y position of the magnetic truck. The X and Y sensors on the housing frame are positioned such that X home position of the truck is sensed first, and then its Y home position is sensed.

Figure 9:
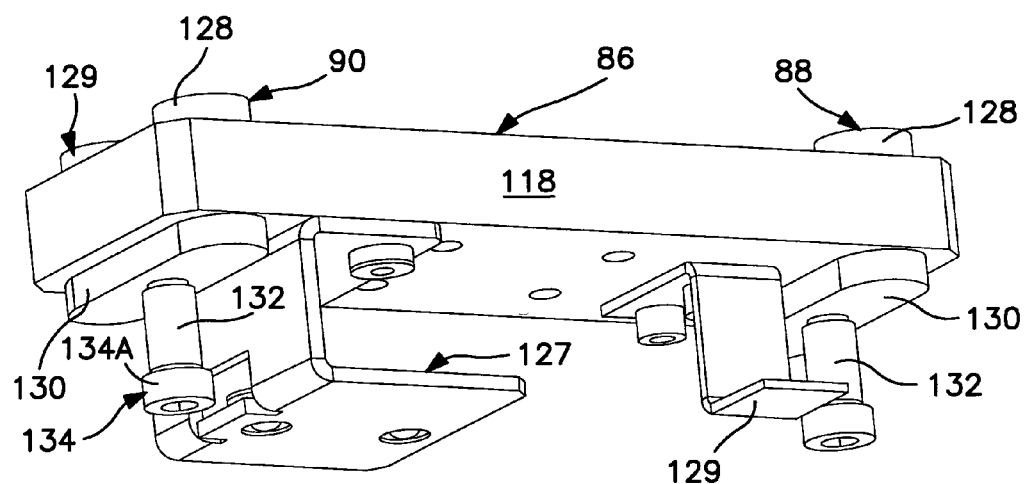
FIG. 9 is an enlarged bottom perspective view of the magnetic X/Y truck used in the FIG. 7 apparatus to magnetically engage a specimen-container rack.

Still referring to FIG. 9, each of the permanent magnets 88 and 90 comprises a pair of cylindrical bar magnets 128, 129, that are connected by a flux bridge 130. The bar magnets are received by cylindrical bore holes formed in plate 118, and they are positioned such that opposite magnetic poles (north/south) extend above the plate surface. The permanent magnets are biased upwardly by a spring 132 that surrounds a shoulder screw 134, threaded into the base of plate 118 and extending downwardly, through a clearance hole formed in the flux bridge. One end of the coil springs is supported by the bolt head 134A, and the opposite end of the spring engages the flux bridge and thereby urges the flux bridge into contact with the underside of plate 118. Preferably, each of the bar magnets has a diameter of about 9.5 mm., and magnets are spaced apart by about 19 mm., center-to-center. The length of each magnet is such as to protrude about 3 mm above the plate 118 when the flux bridge contacts the underside of the plate. Preferably, each of the magnets comprises neodymium-doped iron. The flux bridge is made of iron and is about 6 mm. in thickness. Preferably, the X/Y drive system 70 is positioned so that a spacing of about 1 mm. is provided between the top of the bar magnets and the bottom of the rack-support plate P.

In the X/Y drive mechanism described above, it should be noted that the spacing between the permanent magnets carried by the magnetic truck 86 and the bottom surface of plate P can be maintained substantially constant throughout the X/Y movement of the truck. This attribute of the system results from the rigid mounting scheme, utilizing rigid shafts or rods 72, 74 and the rail 112, for supporting the truck as it moves. Contrast this mounting scheme with the prior art scheme for moving magnets in a linear magnetic transport system drive where flexible belts support the magnets for "linear" movement. Thus, the system described herein provides a substantially uniform magnetic force between the racks and the magnetic field-producing device no matter where the device is in the X/Y plane.

Figure 11A:
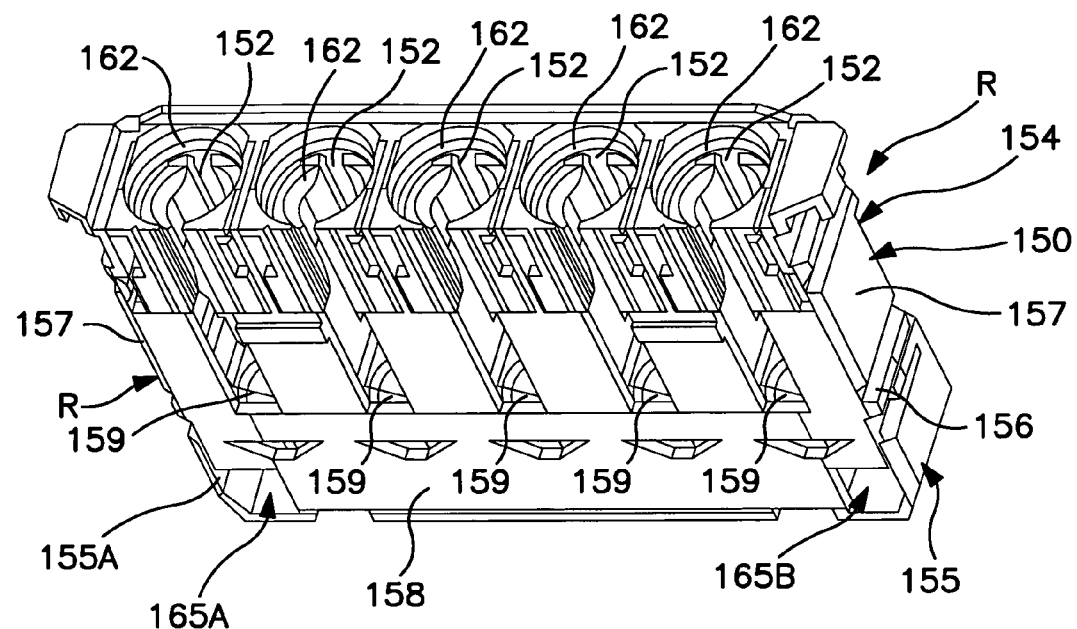
FIGS. 11A and 11B are top-front side and bottom-rear side perspective views, respectively, of a preferred specimen-container rack adapted for use with the magnetic specimen-transport system shown in FIG. 7.
Figure 11B:
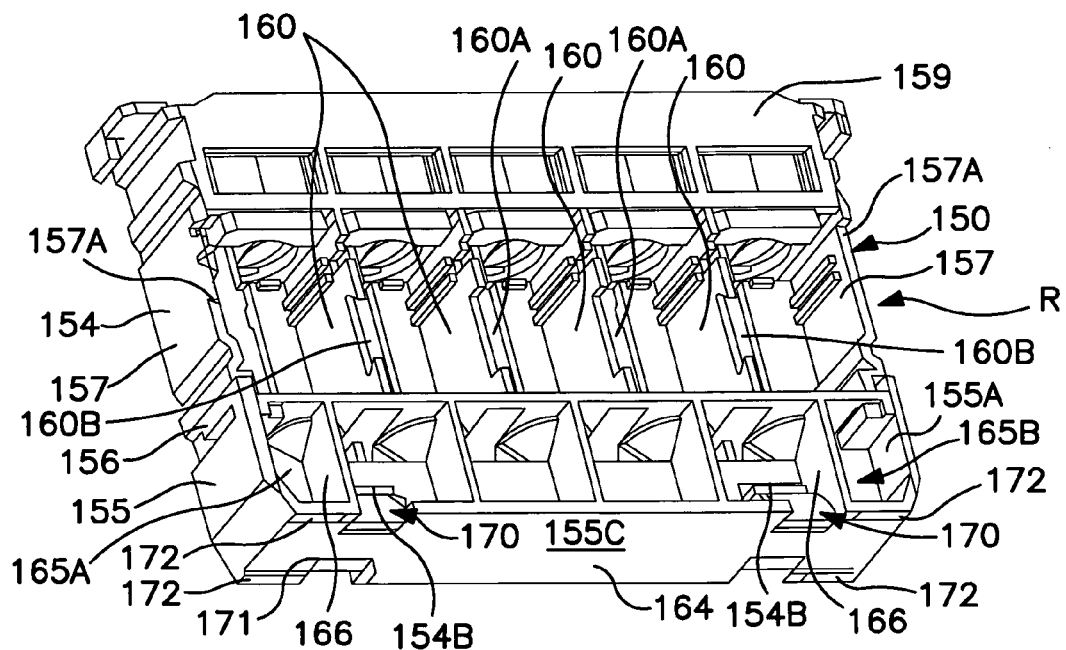

Referring now to FIGS. 10, 11A, 11B and 12, a preferred specimen-container rack R adapted for use with the magnetic specimen-transport apparatus described above is shown as comprising a housing 150 that defines plural (in this case five) compartments 152 for receiving a like plurality of specimen containers C. In the embodiment shown, housing 150 is made of injection-molded plastic and comprises two interlocking sections, an upper section 154 that defines the container compartments 152, and a base section 155 that provides support for the specimen containers received by the rack, and further serves to house and support the above-noted magnetically-attractive members 170. The two sections are snapped together and held in place by a pair of flexible arms 156 provided at opposite ends of the base section. In FIGS. 11A and 11B, the upper section of the rack is shown as comprising a pair of parallel end walls 157 which extend between the rack's forward side wall 158 and its rear side wall 159 at opposite ends of the rack. A plurality of equally-spaced transverse walls 160 also extend between the front and rear walls. These transverse walls operate to define each the container compartments 152. At the top of each compartment 152, a container-centering assembly 162 is provided. The latter serves to releasably engage specimen containers of different diameters within the compartments, whereby the central longitudinal axes of the received containers are equally spaced and arranged in parallel in a common plane. Thus, when such a specimen-container rack is registered in its specimen-aspiration position within a specimen-transport module, the aspiration probe assembly can repeatedly and reliably access the center of each of the specimen containers by moving sideways (along the X coordinate) in a vertical plane. Details of the centering assemblies 162 are described in the commonly assigned U.S. Pat. No. 5,687,849, incorporated herein by reference. The engaging force between the container-centering assembly and the container is sufficient to prevent the container from rotating or moving axially during the specimen-mixing operation when the containers are repeatedly inverted.

Figure 12:
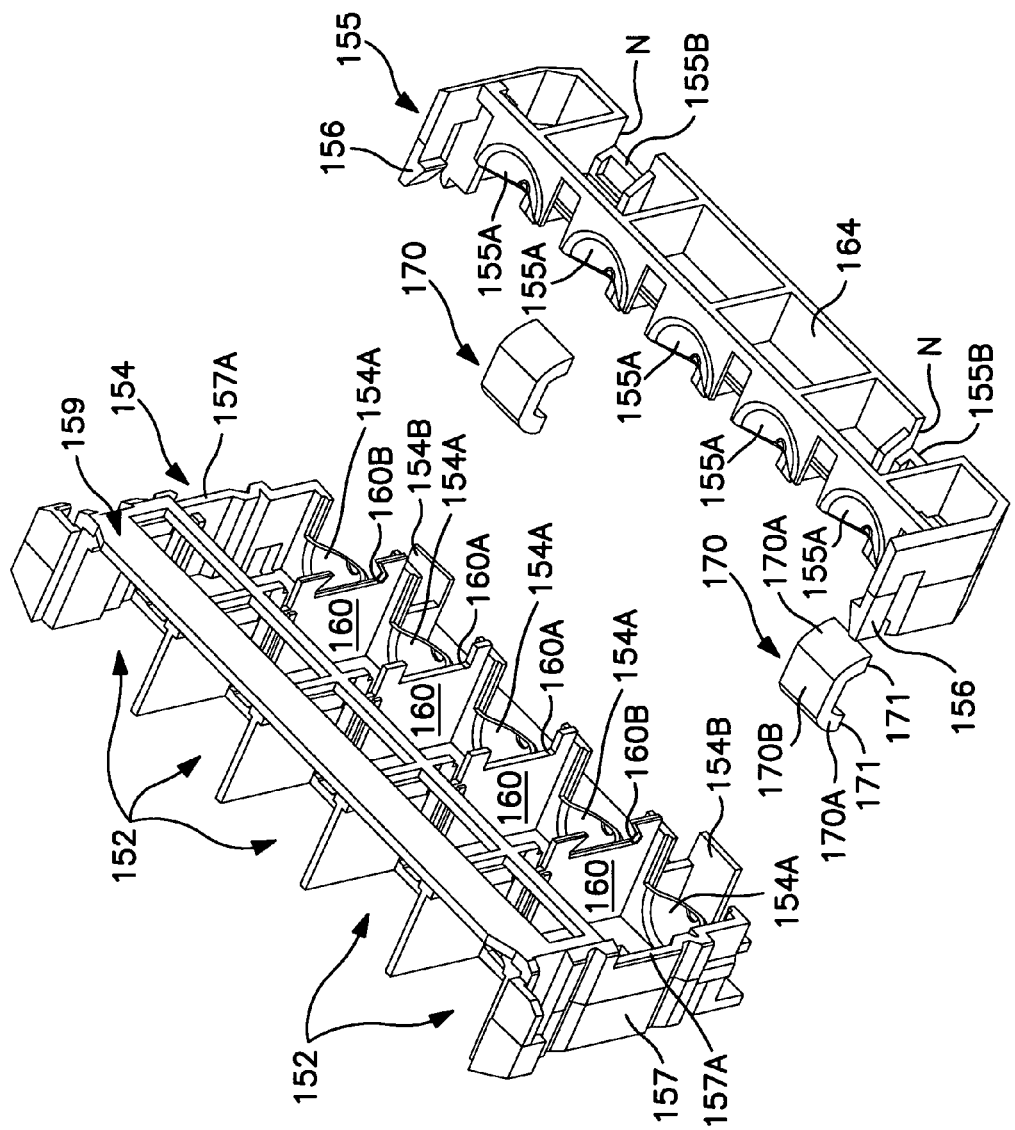
FIG. 12 is an exploded perspective view of the rack shown in FIGS. 11A and 11B.

As shown in FIGS. 11B and 12, the rear, vertical edge of walls 157 and 160 are provided with structure that accommodates a horizontally-extending tongue member 47A (shown in FIG. 13) that protrudes from the mounting plate 47 of the mixing device 46. Such accommodating structure takes the form of series of spaced notches 157A, 160A and 160B. Whereas notches 157A and 160A are rectangular in shape and provide clearance for the tongue member 47A, notches 160B have a trapezoidal shape that is adapted to engagingly receive the opposing edges of the tongue member 47A (which has a trapezoidal transverse cross-section), as the rack is caused to slide horizontally along the surface of mixing plate 47 by the magnetic transport system described above. Preferably, the trapezoidal notches are formed in the edges of walls 160 that separate the first and second compartments 152, and the forth and fifth compartments 152. The dimensions of the rectangular notches 157A and 160A are such as to enable the tongue member 47A to slide unimpededly along wall 47 to engage the notches 160B. Upon completing engagement between the two notches 160B and tongue 47A, the specimen-container rack is releasably locked in a position to be inverted by the mixing device 46, causing the contained specimens in the rack to be mixed, and to have the aspiration probe assembly PA of an associated clinical instrument access any one of the specimen containers supported by the rack. The rack is further secured to the mixing plate by a magnetic force between a permanent magnet 186 carried by the mixing plate and a magnetically-attractive member 170 carried by the rack and used to magnetically transport the rack atop surface S, as explained above. The details of the specimen mixer are discussed further below.

When the two rack components 154 and 155 are snapped together, a pair of conical sections 154A and 155A formed in each of the components 154 and 155, respectively, combine to form a cone-shaped support 159 for each specimen container in the rack. Such a conical support prevents the containers for moving axially downwardly during specimen aspiration. Further, they serve to center the lower part of the specimen-container within the specimen compartments 152. The base section 154 further defines a pair of pockets 165A and 165B at opposite ends of the rack. These pockets are positioned to receive a movable drive member 290A associated with the redundant drive mechanism (shown in FIGS. 17 and 18) that is located in the front module housing 60. As explained below, after such member has entered on of the pockets 165A or 165B and is caused to move laterally (in the X-direction), the rack will be physically pulled along path F by the force exerted by the drive member on the inside of the rack's end wall 157.

In order to render the rack susceptible to being advanced on surface S by the underlying magnetic transport mechanism described above, the base section 155 of rack housing 150 is structured to receive and support a pair of U-shaped, magnetically-attractive members 170 (best shown in the exploded view of FIG. 12). Preferably, each member 170 comprises a ferromagnetic material, most preferably magnetically-attractive stainless steel 440C. Each member 170 comprises a pair of spaced leg portions 170A that are connected at together at one end by a bridge portion 170B. Members 170 are supported in the rack's base portion so that the distal ends 171 of their respective leg portions 170A extend downwardly, toward the bottom surface 155B of the rack. The concave portion of each member 170 is supported and appropriately positioned by an integral structure 155B formed in the bottom of the base section 155. As shown in FIG. 11B, the bottom surface 155C of the rack defines four rectangular pads 172 which protrude downwardly, by about 0.5 mm., at the four corners of the rack. These pads provide the only physical contact between the rack and the transport surface S; thus, the rack slides atop surface S on these four pads. Preferably, structures 155B are dimensioned to support members 170 so that the distal ends 171 of members 170 terminate about 0.5 mm. short of the plane of the pads 172; thus, they terminate in the plane of the rack's bottom surface 155C. Rectangular notches N are formed in the rack's bottom wall 162 to enable the distal ends 171 to extend to the plane of the bottom surface 155C of the base section. A pair of spaced tabs 154B formed on the lower portion of the upper section 154 serves to provide a downward force on the respective top surfaces of the bridge portions 170B of members 170 when the upper and lower sections are snapped together; such force serves to clamp members 170 atop their supporting structures 155B and thereby prevent the distal ends of such members from moving away from their intended position in the plane of the rack's bottom surface 155C. The nominal edge-to-edge spacing between the distal ends 171 corresponds to the nominal edge-to-edge spacing between the pole tips 128 and 129 of the permanent magnets 88 and 90 carried by the magnetic truck 86. Preferably, this spacing is about 9.5 mm. Thus, when a specimen-container rack is resting on its pads 172 atop surface S with the distal ends of members 170 being juxtaposed to the pole tips of magnets 88 and 90, a magnetic circuit will be completed, with the flux emanating from one magnetic pole tip passing through member 170 and entering the opposite pole tip. The strength of the magnetic pole pieces is selected to provide a sufficient magnetic coupling between the rack and the drive mechanism to impart motion to the rack as the magnetic drive moves below surface S. The provision of opposing U-shape structures, one for the permanent magnets 88 and 90 and the other for the magnetically-attractive members 170, gives rise to a magnetic coupling that strongly resists lateral decoupling forces by maximizing the ratio of lateral forces to the vertical forces.

In use, the X/Y magnetic transport system operates under the control of the system controller 20 to initially position the magnetic truck beneath the first rack in the input queue 41, i.e., the rack positioned adjacent the guide member G1 shown in FIG. 4. In doing so, it should be noted that the mechanism used to forwardly advance racks within the input queue can only forwardly advance a single rack to a position in which it would be the third rack back from the guide plate G1. Thus, to assure that the magnetic transport mechanism operates to magnetically capture a rack in the input buffer when only one or two racks are in the input queue, the magnetic transport mechanism will "enter" the input buffer, from below plate P, of course, at a location underlying the third rack from the front. Upon entering the input buffer as noted, the magnetic drive mechanism will magnetically engage the rack in the third rack back position. If the rack engaged is the only rack in the queue, the transport mechanism will advance it into the registration position adjacent guide member G1 by moving in the Y-direction. Thereafter, the transport mechanism will move the rack edgewise along transport path D as described above. If two racks are in the input queue, the transport mechanism will magnetically capture the second rack back in the queue, which will be located in the third rack back position, and it will advance both racks forward, pushing the first rack ahead of the second until the first rack contacts guide member G1, at which point the racks will be prevented from moving further forward. However, the transport mechanism will continue moving forward in the Y-direction, thereby decoupling the transport magnets from their previous interaction with the second rack, and coupling these magnets with the magnetically-attractive members of the first rack. As will be appreciated, in the event that there are three or more racks in the input queue, the same process will be repeated, in which case the transport magnets are coupled and de-coupled twice before they finally couple with the first rack in the queue. Once magnetically coupled to the first rack in the input queue, the magnet transport mechanism remains couple to the rack until the rack reaches its next destination.

Figure 13:
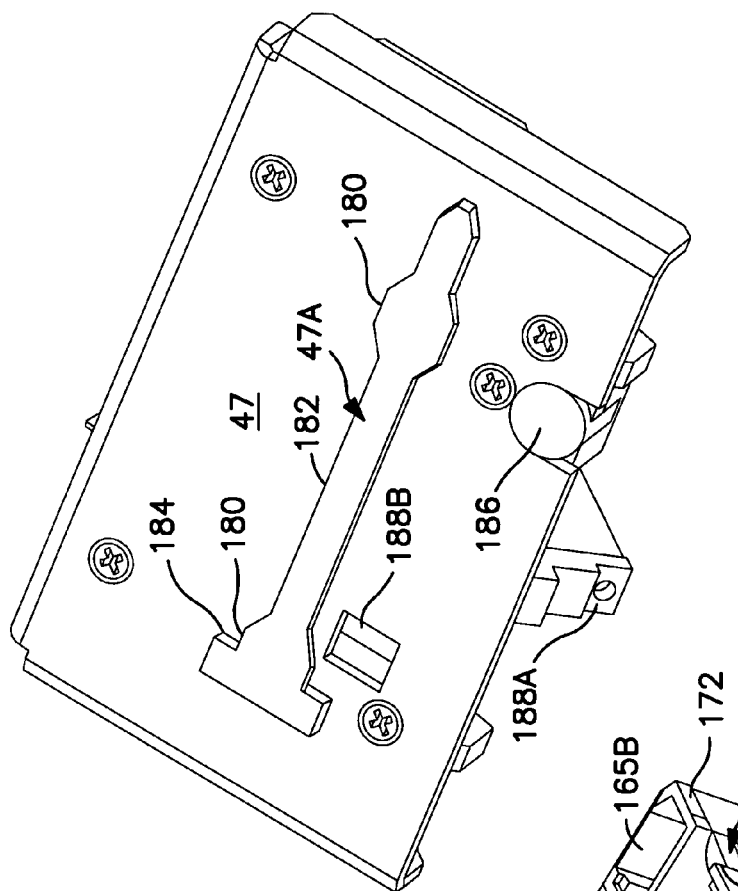
FIGS. 13 and 14 illustrate a preferred mating structure by which a specimen-container rack is operatively coupled to a mixing device of the specimen-transport module of the invention.
Figure 14:
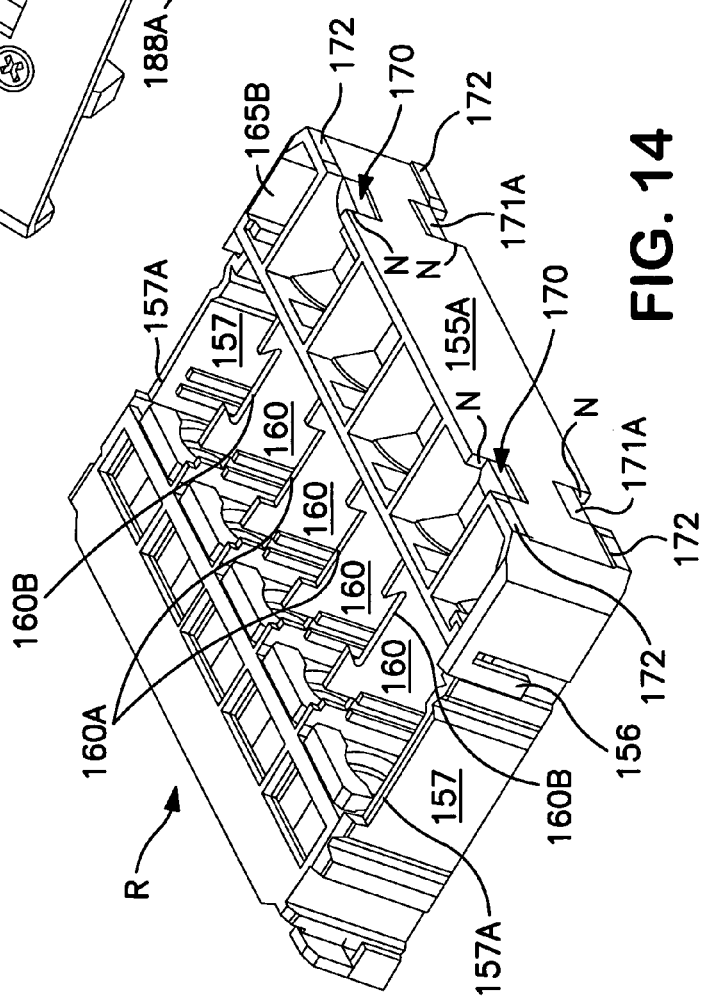

In FIGS. 13 and 14, the preferred tongue-and-groove mechanism by which the mixing device 46 firmly engages each rack for specimen-mixing purposes is more clearly illustrated. As mentioned above, the mixing device 46 comprises a rotatably-mounted plate 47 against which the individual racks are positioned by the X/Y drive mechanism prior to mixing. Prior to mixing, plate 47 is in a vertical plane and thus positioned to receive and be coupled to a rack. As shown in FIG. 13, plate 47 supports a horizontally-extending tongue member 47A having a pair of rack-engaging regions 180 that are separated by a somewhat narrower central region 182. The transverse cross-section of regions 180 is trapezoidal in shape and is of a size adapted to mate with the two notches 160B formed in the rack walls 160 during relative sliding movement between the rack and the surface of plate 47. Such movement, of course, is provided by afore-described drive mechanism 70. A stop surface 184 formed at one of the distal ends of member 47A operates to arrest sliding of a rack along wall 47 by engaging the transverse wall 160 separating the first and second container compartments. At this point, regions 180 are engaged with notches 160B and a permanent magnet 186 mounted on plate 47 magnetically attracts one of the magnetically-attractive members 170 carried by the rack base 155. The position of such magnet is slightly offset (not directly opposite) member 170 so that the magnet exerts a lateral force component acting to urge the stop surface 184 into engagement with the transverse wall that operates to resist further movement of the tongue into the notches 160B. The magnetic attraction between magnet 186 and the magnetically-attractive member 170 is sufficiently strong to prevent the rack from moving laterally on the tongue regions 180 during the mixing operation to follow. Yet, the magnetic interaction between magnet 186 and member 170 is sufficiently weak so as to be readily overcome by the magnetic force exerted on the rack by the X/Y movable magnetic truck when the time comes to disengage the rack from the mixing mechanism. A photoelectric sensor 188A supported by surface S detects racks through a window 188B formed in plate 47 and transmits a signal to the system controller indicating that a rack is positioned on the plate for mixing and that the plate 47 is vertically oriented.

Figure 15A:
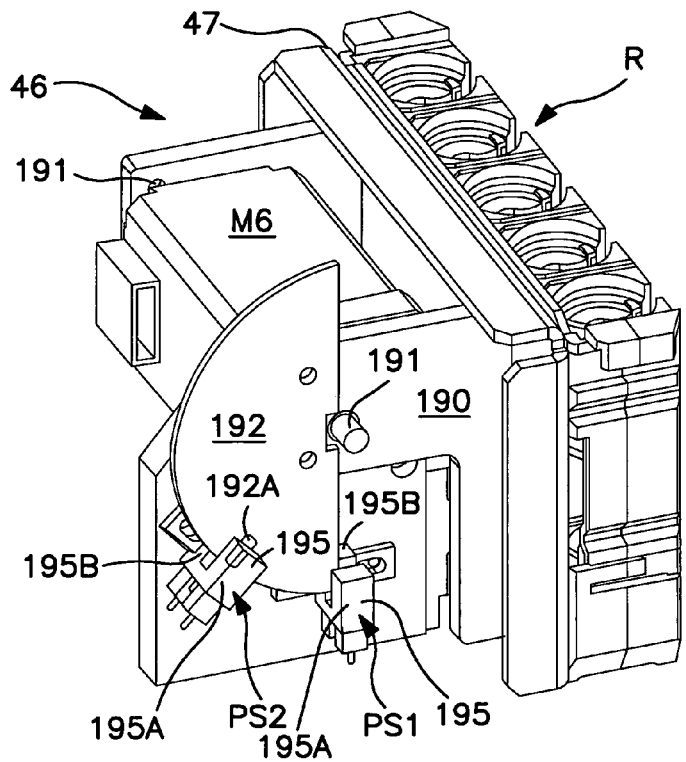
FIGS. 15A and 15B are perspective illustrations of a specimen-mixing device illustrating the position of the specimen-container rack in generally upright and partially inverted positions.
Figure 15B:
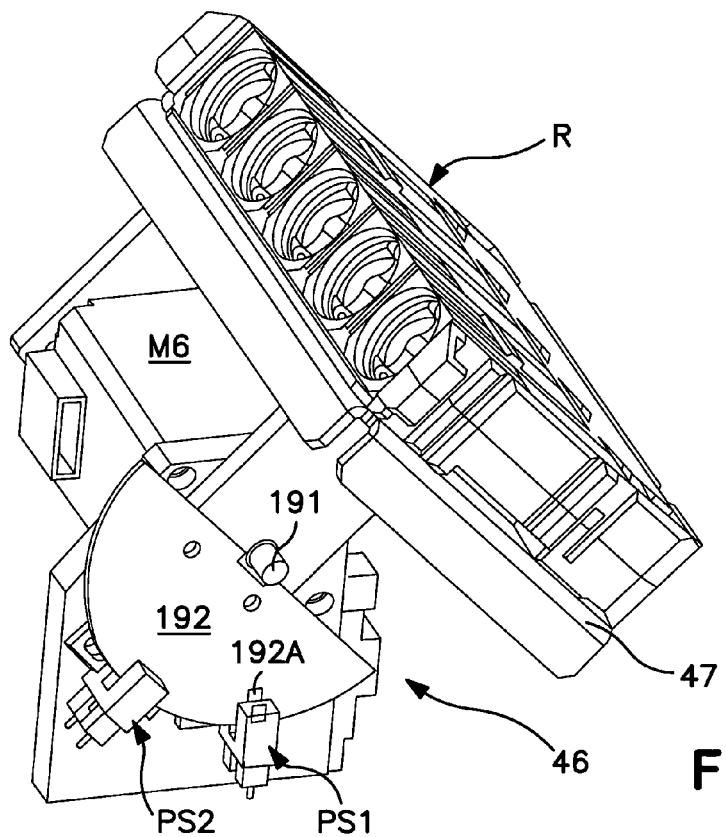
Figure 16A:
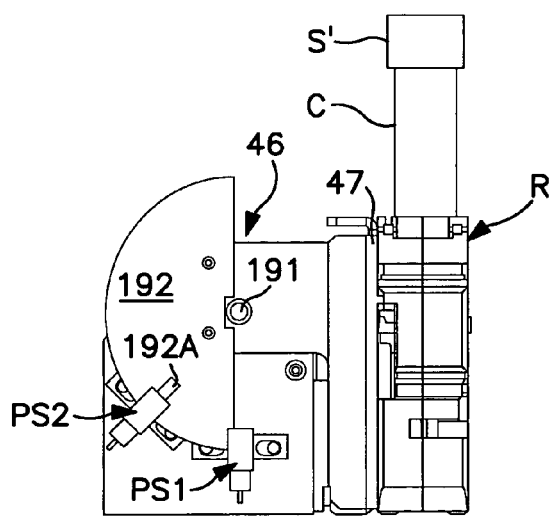
FIGS. 16A-16D are side illustrations of the specimen-mixing device of FIGS. 15A and 15B showing the position of a specimen container rack at four different times during a specimen-mixing operation.
Figure 16B:
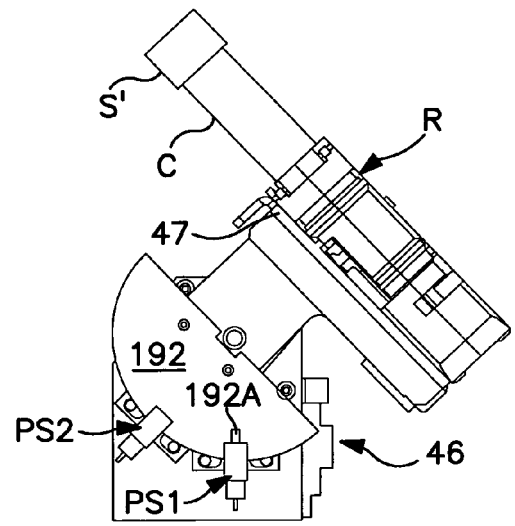
Figure 16C:
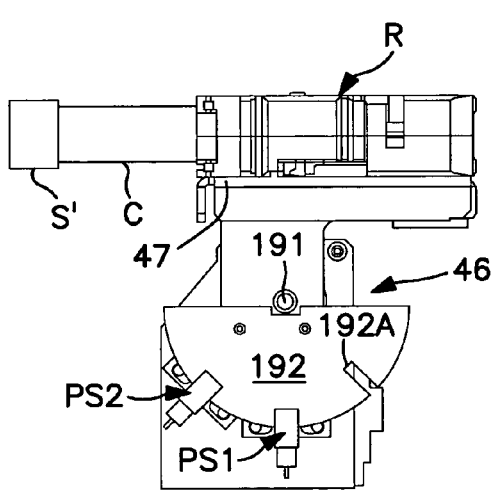
Figure 16D:
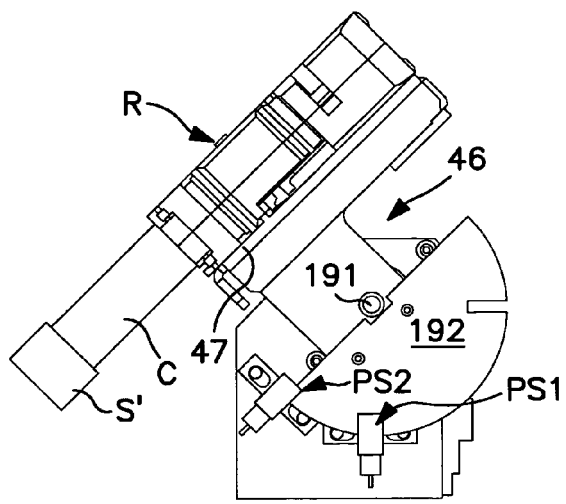

In FIG. 15A, a rack is shown as operatively coupled to the mixing plate 47 prior to mixing. Plate 47 is supported by a yoke assembly 190 that is supported for rotation on the drive shaft 191 of a bi-directional stepper motor M6 that operates under the control of the system controller 20. The angular position of plate 47 as it moves about the drive shaft axis is sensed by a pair of photoelectric sensors PS1 and PS2 The latter are positioned at selected positions about the periphery of a semi-circular disk 192 that is rigidly attached to yoke 190 as the yoke rotates with drive shaft 191. Each photoelectric sensor comprises a yoke-shaped housing 195 that supports a light-emitter and a light-sensor between opposing and spaced arms 195A and 195B. The respective yoke arms of the photoelectric sensors are positioned on opposite sides of the disk 192 in a position to sense the passage of a notch 192A formed in the disk periphery. The photoelectric sensors are angularly spaced by 45 degrees about the disk periphery and located so that, when the rack is in a vertical position, as shown in FIGS. 15A and 16A, both sensor detect light from their respective light emitters, a condition in which both sensors are "ON". PS1 senses the emitted light unobstructed by the disk, and PS2 senses the emitted light as it passes through the notch 192A. When the motor shaft 191 has rotated to a 45 degree "cap-up" position, as shown in FIGS. 15B and 16B, PS1 senses light passing through the notch 192A, and PS2 senses no light since it is blocked by the disk; thus, PS1 is ON, while PS2 is OFF. As the drive shaft continues to rotate counterclockwise, as viewed in FIGS. 16A and 16B, both photoelectric sensors are in an OFF state until the trailing edge of disk 192 passes sensor PS2, at which time PS1 is OFF while PS2 is ON. At this time the container C has been inverted to a 45 degree "cap-down" position. In the cap-down position, the air bubble in the container will have shifted to the bottom of the container, thereby substantially mixing the liquid specimen in the container. Having reached the cap-down position, the stepper motor reverses, and the container is returned to its 45 degree cap-up position, thereby re-inverting the container and its contents. This cycle is repeated several times. Preferably, a specimen rack is rotated between its cap-up and cap-down positions eight times before a specimen is aspirated from the first container in the rack. While this specimen is being processed, the rack is inverted two more times, and this process is continued until the last specimen in the rack has been aspirated. Thus, the last specimen to be aspirated in a rack having five containers will be inverted sixteen times prior to aspiration.

Figure 17:
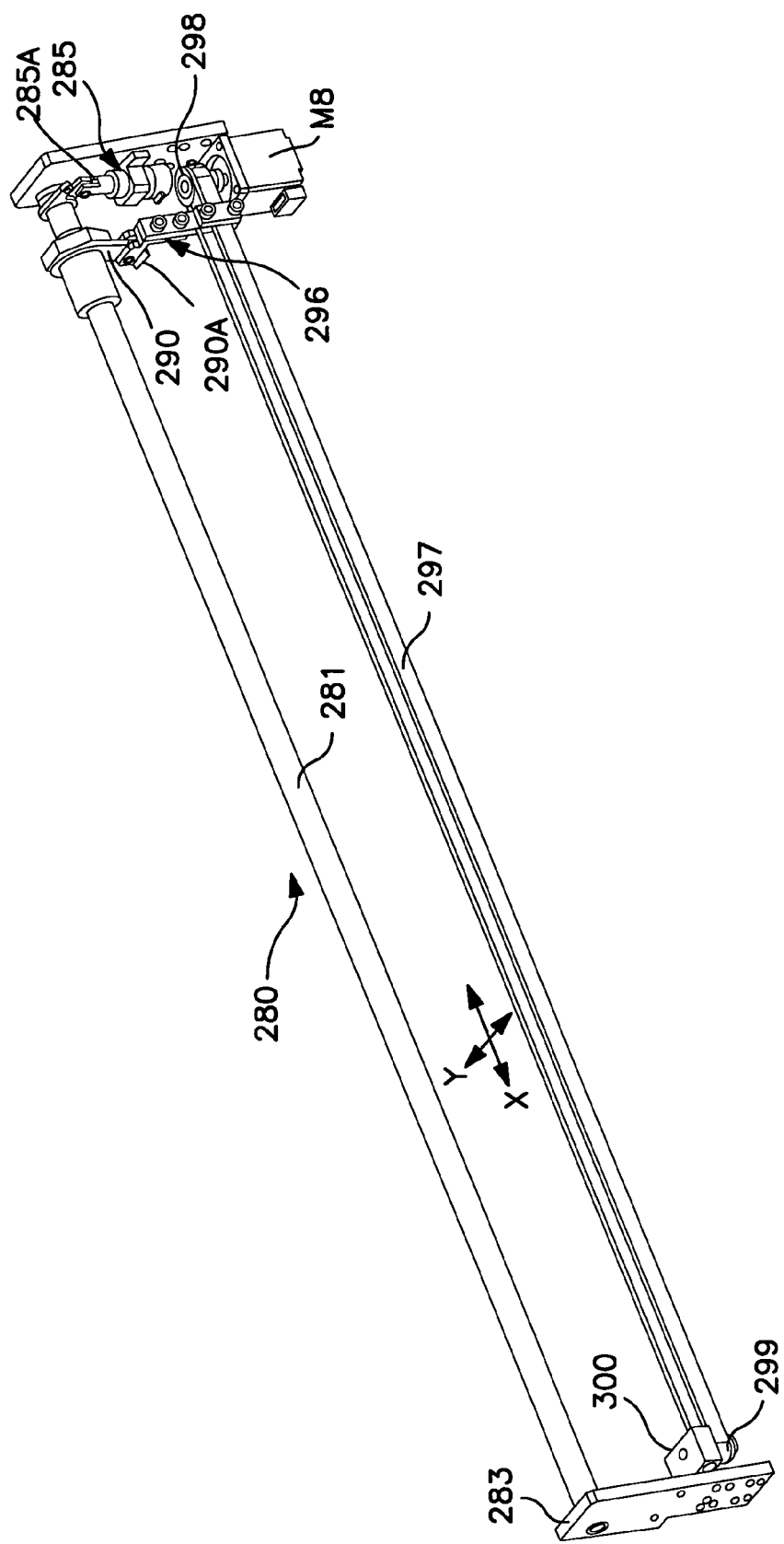
FIGS. 17 and 18 illustrate a preferred redundant drive mechanism for advancing specimen-container racks between adjacent specimen-transport modules.
Figure 18:
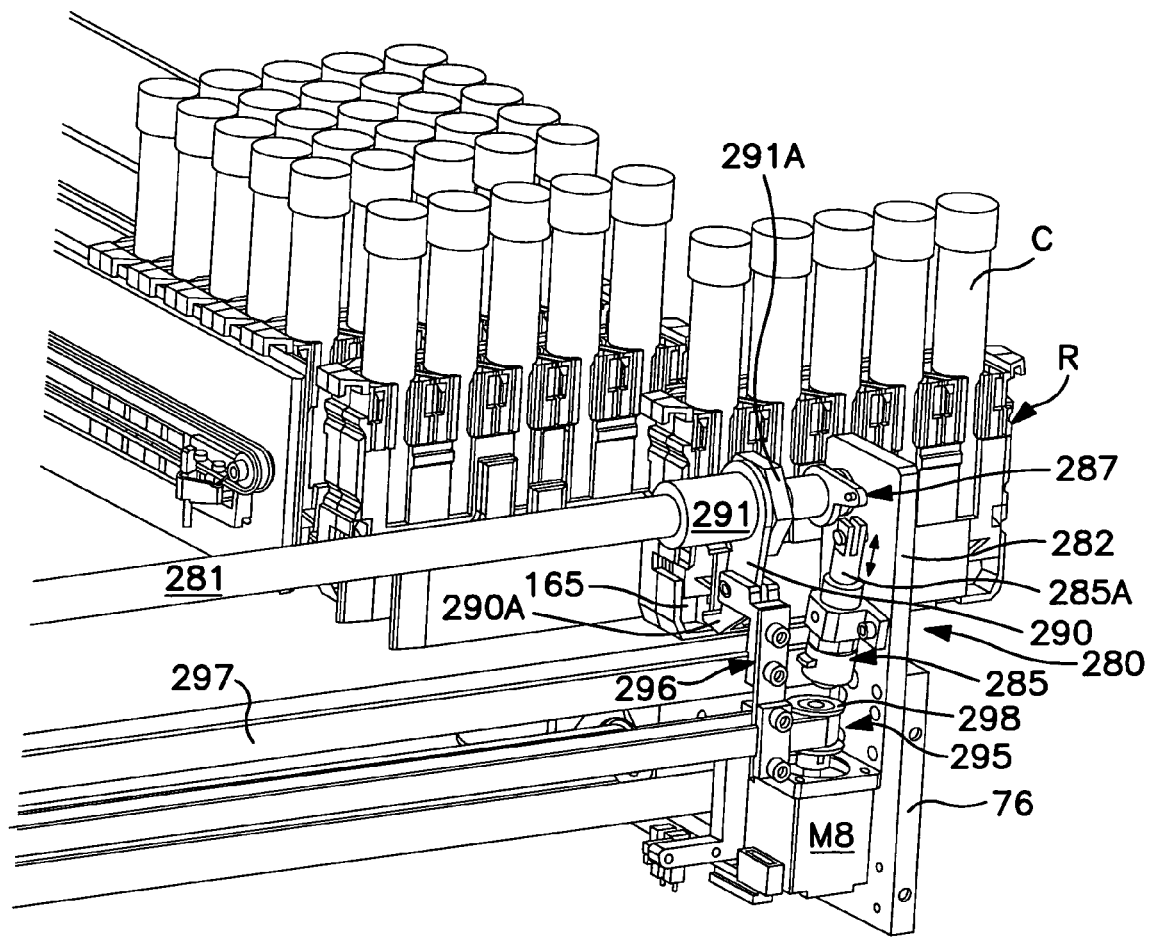

In a workcell environment where several different clinical instruments are transferring specimen-container racks between their respective specimen-transport modules in the manner described above with reference to FIG. 6, circumstances may arise that make it either desirable or mandatory to bypass the X/Y drive mechanism 70 of a particular instrument in order to transport a specimen-container rack from one instrument to another. For example, in a three instrument workcell where the X/Y drive mechanism of the middle instrument is not functioning, it is desirable to provide the workcell with the capability of continued operation of the processing needs of a given sample. Thus, in accordance with another aspect of this invention, a redundant drive mechanism 280, illustrated in FIGS. 17 and 18, is provided in each specimen-transport module for advancing a specimen-container rack through the module, from one of its rack-transfer stations to another, independently of the X/Y transport mechanism of the module. Such redundant drive mechanism is housed within the forward housing 60 of each module, and it extends between the rack-transfer stations 52 and 54.

Referring to FIG. 17, drive mechanism 280 comprises a spline shaft 281 of non-circular (e.g., star-shaped) transverse cross-section. The spline shaft extends between a pair of parallel support plates 282 and 283 which are rigidly connected to the module side walls 76 and 78. Plates 282 and 283 contain bearings that serve to rotatably support the spline shaft for rotation about its longitudinal axis. The rotational position of shaft 281 is controlled by a linear actuator 285 mounted on wall 282. Actuator 285 comprises a linear actuator member 285A which moves axially between an extended position, shown in FIG. 23, to an unextended position closer to the linear actuator housing. A mechanical linkage 287 connects the actuator with the spline shaft 281. Thus, as the linear actuator moves about 12 mm.

between its extended and non-extended positions, the spline shaft rotates through an angular range of about 30 degrees. The spline shaft slidably supports a plate 290 having a rack-engaging foot member 290A. Plate 290 is provided with a central opening (not shown) that is shaped to receive and slidingly engage the spline shaft. Plate 290 is clamped between the spline shaft truck 291 and a nut 291A, both of which are slidably supported by the spline shaft and adapted to rotate therewith. Thus, when the spline shaft is caused to rotate by the retracting movement of the linear actuator, plate 290 will rotate with the shaft and, in doing so, foot portion 290A will move in the Y direction, towards the rear of the module. If a specimen container rack R is positioned as shown in FIG. 18, the foot. Member 290A of plate 290 will enter one of the rack-pockets 165A or 165B. Since the width of the foot 290A is considerably less than the width of the rack-pocket, it is a relatively easy task in practice for the foot to enter the pocket. Upon entering the rack-pocket, the foot portion is now ready to drivingly engage the side wall of the pocket and thereby advance the rack along path F of the specimen-transport module. When the linear actuator member moves to its extended position, the spline shaft will rotate in the opposite (counter-clockwise) direction causing foot member 290A to move out of the rack-pocket, to a position that enables the spline shaft truck to move unimpededly along the spline shaft.

To advance a rack along path F, plate 290 is slidably driven along the spline shaft by a belt-drive system 295. The belt drive system comprises a bi-directional stepper motor M8 that is mounted on the module side wall 76. Motor M8 is controlled by the system controller 20 and operates to selectively advance an endless belt 297 that is trained about a drive pulley 298 and an idler pulley 299. The drive pulley is mounted on the drive shaft of the stepper motor, and the idler pulley 299 is mounted for rotation on a fixed shaft supported by the base of a belt-tensioner housing 300 mounted on the shaft-support plate 283. As shown, belt 297 extends in the X-direction, parallel to path F of the module. Plate 290 is mechanically connected to the drive belt via a linkage 296.

In operation, the redundant drive mechanism 280 can be used to bypass a module by mechanically advancing a rack from the position shown in FIG. 23, i.e., in a position in which the rack R spans the opposing transfer stations of adjacent specimen-transport modules, (e.g., stations 52 and 54 in FIG. 6) and along path F, shown in FIG. 6, to a similar "spanning" position on the opposite side of the module. Having reached this second position, the so-transported rack will be acted upon by the X/Y drive mechanism, or the redundant drive mechanism, of the adjacent module. In advancing a rack along path F, foot portion 290A of plate 290 enters one of the rack pockets (the more inboard pocket) in the manner described above. As belt 297 is driven in the X-direction, plate 290 will be slidably driven along the spline shaft 281, and the lateral surface of foot portion 290A will exert a driving force on the end wall of the rack pocket, causing the rack to be pulled along surface S and move along path F. When plate 290 reaches the end of its travel at the opposite side of the module, the specimen-container rack will be located such that the leading edge of the rack will only have reached the edge of the module. At this point, the spline shaft will be rotated in the opposite direction so as to remove the foot member 290A from engagement with the rack. The belt drive 295 will operate in the reverse direction to position plate 290 behind the trailing edge of the rack. Then, the spline shaft will rotate again in the opposite direction to fully extend the foot member again, and the belt drive will again be reversed to drive the plate in the forward direction along the spline shaft. In doing so, the extended foot portion will drivingly engage the rear edge of the rack and thereby act to push the rack until the rack has advanced to the module-spanning position shown in FIGS. 6 and 23, this time on the opposite side of the module. The rack is then in a position to be advanced further by the adjacent module in the manner described above. Being able to bypass a module of a multi-instrument workcell in the manner described allows the workcell instruments to remain connected, even when one of the transport modules of an instrument experiences a failure of either one of its rack-transport systems. This redundancy of the rack drive adds to the overall availability of the workcell, and it reduces the level of operator intervention.

From the foregoing, it will be appreciated that a new and advantageous specimen-container rack has been devised that is particularly well-suited for use with a rack-transport mechanism of the type described above. It will be appreciated that the disclosed structural details of the rack (e.g., the size, shape and location of the magnetically-attractive members 170, the size and location of the transport pockets 165A and 165B, and the configuration and location of notches 160B) are specific to the particular transport/mixing apparatus disclosed, and that certain variations can be made in these details without departing from the spirit of the invention; thus, resort should be had only to the appended claims in determining the scope of the invention.

What is claimed is:

1. A specimen-container rack adapted for use with a magnetic transport mechanism designed to produce a moving magnetic field atop a rack-supporting surface for the purpose of advancing individual specimen-container racks in mutually-perpendicular directions atop said surface, said specimen-container rack comprising:
    (a) a rack housing comprising (i) an upper section for receiving, aligning and spacing a plurality of specimen-containers, and (ii) a base section operatively connected to the said upper section and having a bottom surface adapted to slidingly engage said rack-supporting surface, said base section serving to support said upper section so that said containers are in a generally upright orientation, and
    (b) a pair of U-shaped, magnetically-attractive members, each U-shaped member comprising a pair of spaced leg-members connected together by an integral bridging portion, each of said leg members having a distal end spaced from said bridging portion, each of said U-shaped members being supported at spaced nominal positions on said base section in which the respective leg members depend downwardly towards said bottom surface of the base section, and in which said distal ends of said leg members terminate in a plane closely spaced from the bottom surface of said base section.

2. The specimen-container rack as defined by claim 1 wherein said bottom surface of said base section comprises a planar portion and a plurality of spaced elevated areas extending outwardly from said planar portion and serving as rack-support pads on which said rack slides atop said rack-support surface.

3. The specimen-container rack as defined by claim 1 wherein said housing comprises at least one tab mounted on said upper section for urging said U-shaped members towards said nominal positions when said upper section and base section are operatively connected.

4. The specimen-container rack as defined by claim 1 wherein said upper and base sections of said frame are discrete components that matingly engage and retained together by flexible members carried by one of said sections.

5. The specimen-container rack as defined by claim 1 wherein one of said frame sections defines a pair of pockets formed in a side wall thereof of said frame, said pocket being adapted to receive a movably driven member associated with a transport system to physically advance said rack edgewise atop said surface.

6. A specimen-container rack adapted for use with a magnetic transport mechanism designed to produce a moving magnetic field atop a rack-supporting surface for the purpose of advancing individual specimen-container racks in mutually-perpendicular directions atop said surface, said specimen-container rack comprising:
  (a) a rack housing comprising (i) an upper section for receiving, aligning and equally-spacing a plurality of specimen-containers, and (ii) a base section operatively connected to the said upper section and having a bottom surface adapted to slidingly engage said rack-supporting surface, said base section serving to support said upper section so that said containers are in a generally upright orientation, and
  (b) a pair of U-shaped, magnetically-attractive members, each U-shaped member comprising a pair of spaced leg-members connected together by an integral bridging portion, each of said leg members having a distal end spaced from said bridging portion, each of said U-shaped members being supported at spaced nominal positions on said base section in which the respective leg members depend downwardly towards said bottom surface of the base section, and in which said distal ends of said leg members terminate in a plane closely spaced from the bottom surface of said base section,
  wherein said upper section of said rack housing comprises first and second spaced side walls interconnected by a pair of end walls and a plurality of transverse walls intermediate said end walls that collectively define a plurality of equally-spaced container compartments, and wherein a plurality of notches are formed in the edges of at least two transverse walls for receiving and retaining structure associated with a specimen-mixing device adapted to lift and invert a rack for the purpose of mixing specimens within said containers.

7. The specimen-container rack as defined by claim 6 wherein each of said notches has a trapezoidal shape.

8. A magnetically-attractive specimen-container rack adapted for use with a magnetic transport system for transporting racks of specimen-containers to or within an automated clinical instrument for analysis and/or processing, said specimen-container rack comprising a pair of U-shaped magnetically-attractive members mounted in a base section of a rack housing so that distal ends of said U-shaped members extend towards a base surface of said rack and terminate slightly short of the plane in which said rack is supported for movement atop a rack-supporting surface, said members being adapted to cooperate with similarly-shaped permanent magnets carried by an X/Y-movable truck that underlies a non-magnetic rack-supporting plate.

9. The specimen-container rack as defined by claim 8 further comprising structure defining a pair of laterally spaced side-pockets formed in one side of said rack, said side pockets serving to receive a movably-mounted member associated with a liner drive mechanism by which said rack can be physically advanced edgewise along a liner path.

10. The specimen-container rack as defined by claim 8 further comprising notch structure formed in a side wall of said rack by which said rack can be releasably engaged in order to lift and invert said rack to effect mixing of contained specimens.

* * * * *